(12) United States Patent
Seo et al.

(10) Patent No.: US 10,806,704 B2
(45) Date of Patent: Oct. 20, 2020

(54) MULTILAYERED EMULSION FILM AND METHOD FOR PREPARING THE SAME

(71) Applicant: INDUSTRY-UNIVERSITY COOPERATION FOUNDATION HANYANG UNIVERSITY ERICA CAMPUS, Ansan-si, Gyeonggi-do (KR)

(72) Inventors: Hyemin Seo, Gyeonggi-do (KR);
Kyounghee Shin, Gyeonggi-do (KR);
Jinyong Lee, Gyeongsangnam-do (KR);
Jin Woong Kim, Gyeonggi-do (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 16/199,863

(22) Filed: Nov. 26, 2018

(65) Prior Publication Data
US 2019/0160018 A1    May 30, 2019

(30) Foreign Application Priority Data

Nov. 27, 2017 (KR) .................. 10-2017-0159471
Nov. 15, 2018 (KR) .................. 10-2018-0140542

(51) Int. Cl.
*A61K 9/70* (2006.01)
*A61K 9/107* (2006.01)
(Continued)

(52) U.S. Cl.
CPC .......... *A61K 9/7007* (2013.01); *A61K 9/0002* (2013.01); *A61K 9/1075* (2013.01);
(Continued)

(58) Field of Classification Search
None
See application file for complete search history.

(56) References Cited

FOREIGN PATENT DOCUMENTS

| KR | 10-1540066 B1 | 7/2015 |
|----|----|----|
| KR | 101880360 B1 * | 8/2018 |

OTHER PUBLICATIONS

Park et al, Soft Matter, 2018, 14, 5581, (Year: 2018).*
(Continued)

*Primary Examiner* — Celeste A Roney
(74) *Attorney, Agent, or Firm* — Sughrue Mion, PLLC

(57) ABSTRACT

Multilayer thin emulsion films are disclosed. Also disclosed are methods for preparing the multilayer thin emulsion films. According to the methods, an amphiphilic block polymer is used as a surfactant to form a polymer thin film at the oil/water interface, ionic lecithin is used as an auxiliary surfactant to prepare physically stable ionic oil-in-water nanoemulsions, and a layer-by-layer assembly technique is used to alternately laminate polymer thin films and nanoemulsion layers. The multilayer thin emulsion films enable slow release of active substances in specific temperature ranges and are structurally biocompatible while possessing improved capture efficiency and physically stable membrane structures. Spinodal decomposition of the multilayer thin emulsion films is induced by heating, allowing release of oils and active substances loaded into the nanoemulsions. Therefore, the multilayer thin emulsion films are expected to be useful as smart drug release materials in a variety of applications, including cosmetics, pharmaceuticals, and biotherapy.

20 Claims, 21 Drawing Sheets

(51) Int. Cl.
  *A61K 9/00*    (2006.01)
  *A61K 31/07*   (2006.01)
  *A61K 47/24*   (2006.01)
  *A61K 47/36*   (2006.01)
  *A61K 47/34*   (2017.01)
  *A61K 9/127*   (2006.01)

(52) U.S. Cl.
  CPC ............ *A61K 9/1274* (2013.01); *A61K 31/07* (2013.01); *A61K 47/24* (2013.01); *A61K 47/34* (2013.01); *A61K 47/36* (2013.01)

(56) References Cited

OTHER PUBLICATIONS

Rodriguez et al (Soft Matter, 2018, 14, 239) (Year: 2018).*
Bogdanov et al (Polymer, 39(8-9), 1998, 1631). (Year: 1998).*
"The Polymer Society of Korea", DBpia, 2017, 3 pages.

* cited by examiner

MULTILAYERED EMULSION FILM AND METHOD FOR PREPARING THE SAME

BACKGROUND OF THE INVENTION

Field of the Invention

The present invention relates to multilayer thin emulsion films. More specifically, the present invention relates to smart multilayer thin emulsion films having the function of slowly releasing specific drugs at specific temperatures and methods for preparing the multilayer thin emulsion films on a large scale.

Description of the Related Art

Extensive research has been conducted to develop smart drug carriers that effectively load drugs and release the drugs in specific environments. For example, micelles composed of amphiphilic block polymers for loading hydrophobic drugs and liposomes for loading both hydrophobic and hydrophilic drugs have been developed as drug carriers.

Of these, the micelles composed of amphiphilic block polymers are advantageous in their ability to stably load a wide variety of nano-sized drugs, proteins, DNA, and personal care substances. The liposomes can absorb target cells with high efficiency because their surface characteristics can be easily changed, their particle size can be freely controlled, and their structure consists of phospholipid bilayers similarly to the human cellular wall.

However, the micelles have very low drug loadings, resulting in considerably low capture efficiency. The liposomes have difficulty in controlling drug release due to their lower stability than the micelles.

Under these circumstances, the present inventors have earnestly and intensively conducted research to develop new structures of smart particles or thin films that release oils or drugs in specific temperature ranges and are structurally biocompatible while possessing improved capture efficiency and physically stable membrane structures, and as a result, succeeded in preparing new structures of multilayer thin emulsion films.

PRIOR ART DOCUMENTS

Patent Documents

Patent Document 1: Korean Patent Publication No. 10-2010-0040783

SUMMARY OF THE INVENTION

Therefore, the present invention has been made in an effort to solve the above problems, and it is one object of the present invention to provide a multilayer thin emulsion film including a thin layer of oil-in-water emulsions prepared using an amphiphilic block polymer as a surfactant and lecithin as an auxiliary surfactant, achieving physical stability and enabling effective release of an active substance at a specific temperature.

It is a further object of the present invention to provide a new structure of a multilayer thin emulsion film including nanofiber layers, achieving a 1.5- to 2-fold lower release rate of an active substance over a long time.

It is another object of the present invention to provide methods for preparing the multilayer thin emulsion films on a large scale.

One aspect of the present invention provides a multilayer thin emulsion film including a substrate and 1 to 100 layers of composite thin films laminated on the substrate to release an active substance in a specific temperature range wherein each of the composite thin films consists of a cross-linkable positively charged polymer layer coated on the substrate surface and a nanoemulsion layer including a plurality of nanoemulsions arrayed on the polymer layer and wherein each of the nanoemulsions is a spherical particle consisting of (a) a core including the active substance and an oil and a shell including (b) an amphiphilic polymer consisting of a hydrophobic polymer and a hydrophilic polymer and (c) lecithin and continuously or discontinuously surrounding the core.

The oil may be selected from the group consisting of silicone emulsifiers, O/W emulsifiers, ester oils, silicone oils, hydrocarbon oils, waxes, natural oils, liquid animal and vegetable oils and fats, and mixtures thereof.

The amphiphilic block copolymer may be a polyethylene glycol (PEG)-polycaprolactone (PCL) copolymer having polycaprolactone (PCL) as a hydrophobic block and polyethylene glycol (PEG) as a hydrophilic block.

The amphiphilic block copolymer may have a molecular weight of 100 to 100,000 daltons and a degree of polymerization of 1.0 to 1.5.

The polycaprolactone and the polyethylene glycol may be present in a weight ratio of 1-1.5:1 in the amphiphilic block copolymer.

The nanoemulsions may have an average particle diameter of 0.1 to 100 μm.

The amount of the oil loaded into the cores of the nanoemulsions may be from 1 to 10 parts by weight, based on 100 parts by weight of the nanoemulsions.

The amount of the cores including the active substance and the oil may be from 0.2 to 1.0 part by weight, based on 100 parts by weight of the thin emulsion film.

The positively charged polymer may be selected from the group consisting of polyallylamine hydrochloride, polyethyleneimine, polylysine, polydimethyldiallylammonium chloride, and chitosan.

The substrate may be negatively charged by plasma treatment.

A further aspect of the present invention provides a multilayer thin emulsion film including a substrate, 1 to 100 layers of first composite thin films, and 1 to 100 layers of second composite thin films wherein the first composite thin films and the second composite thin films are laminated alternately with each other on the substrate, wherein each of the first composite thin films releases an active substance in a specific temperature range and consists of a cross-linkable cationic polymer layer coated on the substrate surface and a nanoemulsion layer including a plurality of nanoemulsions arrayed on the polymer layer, wherein each of the second composite thin films is disposed on the first composite thin film and consists of a cross-linkable cationic polymer layer coated on the surface of the first composite thin film and a nanofiber layer formed on the polymer layer, and wherein each of the nanoemulsions is a spherical particle consisting of (a) a core including the active substance and an oil and a shell including (b) an amphiphilic polymer consisting of a hydrophobic polymer and a hydrophilic polymer and (c) lecithin and continuously or discontinuously surrounding the core.

The oil may be selected from the group consisting of silicone emulsifiers, O/W emulsifiers, ester oils, silicone oils, hydrocarbon oils, waxes, natural oils, liquid animal and vegetable oils and fats, and mixtures thereof.

The amphiphilic block copolymer may be a polyethylene glycol (PEG)-polycaprolactone (PCL) copolymer having polycaprolactone (PCL) as a hydrophobic block and polyethylene glycol (PEG) as a hydrophilic block.

The amphiphilic block copolymer may have a molecular weight of 100 to 100,000 daltons and a degree of polymerization of 1.0 to 1.5.

The polycaprolactone and the polyethylene glycol may be present in a weight ratio of 1-1.5:1 in the amphiphilic block copolymer.

The nanoemulsions may have an average particle diameter of 0.1 to 100 µm.

The amount of the oil loaded into the cores of the nanoemulsions may be from 1 to 10 parts by weight, based on 100 parts by weight of the nanoemulsions.

The amount of the cores including the active substance and the oil may be from 0.2 to 1.0 part by weight, based on 100 parts by weight of the thin emulsion film.

The positively charged polymer may be selected from the group consisting of polyallylamine hydrochloride, polyethyleneimine, polylysine, polydimethyldiallylammonium chloride, and chitosan.

The substrate may be negatively charged by plasma treatment.

The nanofibers may have an average diameter of 0.20 to 0.45 µm and may be present in an amount of 1 to 10 parts by weight, based on 100 parts by weight of the nanofiber layers.

Another aspect of the present invention provides a method for preparing a multilayer thin emulsion film, including: I) mixing a dispersed phase solution with an aqueous suspension to prepare a mixture solution including nanoemulsions; II) modifying the surface of a substrate to negatively charge the substrate surface; III) immersing the substrate in a solution including a positively charged polymer to form a polymer layer; IV) withdrawing the substrate from the solution and immersing the withdrawn substrate in the mixture solution including nanoemulsions to form a nanoemulsion layer on the polymer layer; and V) repeating steps III) and IV) to form 1 to 100 layers of composite thin films.

Yet another aspect of the present invention provides a method for preparing a multilayer thin emulsion film, including: I) mixing a dispersed phase solution with an aqueous suspension to prepare a mixture solution including nanoemulsions; II) modifying the surface of a substrate to negatively charge the substrate surface; III) immersing the substrate in a solution including a positively charged polymer to form a polymer layer; IV) withdrawing the substrate from the solution and immersing the withdrawn substrate in the mixture solution including nanoemulsions to form a first composite thin film in which a nanoemulsion layer is formed on the polymer layer; V) withdrawing the substrate formed with the first composite thin film from the solution and immersing the withdrawn substrate in a solution including a positively charged polymer to form a polymer layer on the first composite thin film; and VI) withdrawing the substrate from the solution and immersing the withdrawn substrate in a mixture solution including nanofibers to form a second composite thin film in which a nanofiber layer is formed on the polymer layer.

According to the methods of the present invention, an amphiphilic block polymer is used as a surfactant to form a polymer thin film at the oil/water interface, ionic lecithin is used as an auxiliary surfactant to prepare physically stable ionic oil-in-water nanoemulsions, and a layer-by-layer assembly technique is used to alternately laminate polymer thin films and nanoemulsion layers. The multilayer thin emulsion films of the present invention enable slow release of active substances in specific temperature ranges and are structurally biocompatible while possessing improved capture efficiency and physically stable membrane structures.

Spinodal decomposition of the multilayer thin emulsion films is induced by heating, allowing release of oils and active substances loaded into the nanoemulsions. Therefore, the multilayer thin emulsion films of the present invention are expected to be useful as smart drug release materials in a variety of applications, including cosmetics, pharmaceuticals, and biotherapy.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Several aspects and various embodiments of the present invention will now be described in more detail.

One aspect of the present invention is directed to a multilayer thin emulsion film including a substrate and 1 to 100 layers of composite thin films laminated on the substrate to release an active substance in a specific temperature range wherein each of the composite thin films consists of a cross-linkable positively charged polymer layer coated on the substrate surface and a nanoemulsion layer including a plurality of nanoemulsions arrayed on the polymer layer and wherein each of the nanoemulsions is a spherical particle consisting of (a) a core including the active substance and an oil and a shell including (b) an amphiphilic polymer consisting of a biodegradable hydrophobic polymer composed of poly(ester) and a hydrophilic polymer composed of poly(ethylene oxide) and (c) lecithin and continuously or discontinuously surrounding the core.

The substrate and the polymer layer are bound together by an attractive electrostatic force. The polymer layer and the nanoemulsion layer are bound together by an attractive electrostatic force. In the thin emulsion film of the present invention, the substrate is negatively charged by plasma treatment, the polymer layer includes a positively charged polymer, and the amphiphilic polymer and the lecithin constitute the surface of the nanoemulsion layer. The substrate and the polymer layer are bound together by an attractive electrostatic force due to their opposite polarities. The polymer layer and the nanoemulsion layer are bound together by an attractive electrostatic force due to their opposite polarities. That is, the polymer layer including the positively charged polymer is not bound to the nanoemulsion layer including the nanoemulsions, but the polymer is directly bound to the nanoemulsions.

Figure 1:
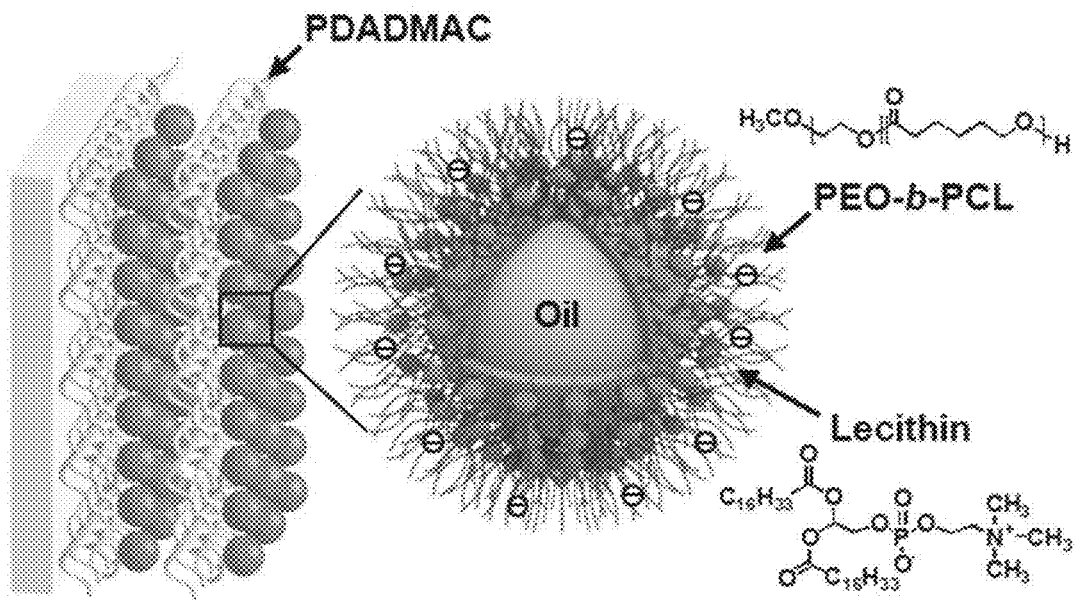
FIG. 1 is a diagram showing the structure of a nanoemulsion and the structure of a thin emulsion film of the present invention.

FIG. 1 is a diagram showing the structure of the nanoemulsion and the structure of the thin emulsion film of the present invention. Referring to FIG. 1, the nanoemulsions are bound to the polymer layer by an attractive electrostatic force because the surface of the nanoemulsions is negatively charged and the polymer of the polymer layer is positively charged. That is, the nanoemulsions are negatively charged by the lecithin and the PEO-b-PCL amphiphilic block copolymer constituting the surface of the nanoemulsions.

The oil is not particularly limited so long as it is usually used in the preparation of oil-in-water nanoemulsions. For example, the oil may be selected from the group consisting of silicone emulsifiers, O/W emulsifiers, ester oils, silicone oils, hydrocarbon oils, waxes, natural oils, liquid animal and vegetable oils and fats, and mixtures thereof. None of these oils affect the release time and rate of the active substance, which was demonstrated through experiments.

Any amphiphilic block copolymer that can form oil-in-water nanoemulsions may be used without particular limitation. The amphiphilic block copolymer may be a polyethylene glycol (PEG)-polycaprolactone (PCL) copolymer having polycaprolactone (PCL) as a hydrophobic block and polyethylene glycol (PEG) as a hydrophilic block. The amphiphilic block copolymer may have a molecular weight ranging from 100 to 100,000 daltons and a degree of polymerization ranging from 1.0 to 1.5. Within these ranges, the amphiphilic block copolymer can be structurally controlled such that the active substance and the oil are slowly released in a desired temperature range (60-80° C.).

The polymer layer improves the durability of the nanoemulsions, making it easy to laminate a large amount of the nanoemulsions thereon. In addition, the polymer layer adheres well to the nanoemulsions, which is advantageous in preventing leakage or loss of the nanoemulsions.

The polycaprolactone and the polyethylene glycol are preferably present in a weight ratio of 1-1.5:1 in the amphiphilic block copolymer. Within this range, the chemical bonding between the polycaprolactone and the polyethylene glycol makes the nanoemulsions highly durable.

The nanoemulsions may have an average particle diameter of 0.1 to 100 µm. If the average particle diameter of the nanoemulsions is less than 0.1 µm, only very small amounts of the active substance and the oil are loaded into the cores. Meanwhile, if the average particle diameter of the nanoemulsions exceeds 100 µm, the durability of the nanoemulsions deteriorates considerably, with the result that the active substance and the oil are released even at low temperatures.

The amount of the oil loaded into the cores of the nanoemulsions is preferably from 1 to 10 parts by weight, based on 100 parts by weight of the nanoemulsions. The loading of the oil in an amount of less than 1 part by weight makes the role of the oil as a carrier meaningless. Meanwhile, the loading of the oil in an amount of more than 10 parts by weight leads to a reduction in the durability of the nanoemulsions, causing the nanoemulsions to collapse.

When the durability, average particle diameter, and preparation processes of the nanoemulsions are taken into consideration, as described above, it is preferred that the amount of the cores including the active substance and the oil is from 0.2 to 1.0 part by weight, based on 100 parts by weight of the thin emulsion film.

The positively charged polymer may be selected from the group consisting of polyallylamine hydrochloride, polyethyleneimine, polylysine, polydimethyldiallylammonium chloride, and chitosan. Polydimethyldiallylammonium chloride is most preferred.

The substrate may be negatively charged by plasma treatment, which enhances the adhesion of the substrate to the polymer layer.

Any active substance that is soluble in the oil and is applicable to skin, mucosa, scalp or hair may be used without particular limitation. Any active substance that can be used in a wide range of applications, for example, cosmetics, drugs, flavors and dyes, and is slowly released into a desired target at a specific temperature may be used.

The cosmetics may include basic cosmetic compositions selected from emulsions, emollients, lotions, creams, packs, gels, patches, and sprays (mists), color tone cosmetic compositions selected from lipsticks, makeup bases, and foundations, cleansers selected from shampoos, rinses, body cleansers, toothpastes, and mouthwashes, and hair cosmetics selected from hair conditioners such as hair tonics, gels, and mousses, hair restorers, and hair dyes. Drugs or quasi-drugs may be applied in the form of lotions, ointments, gels, creams, patches or sprays.

A further aspect of the present invention is directed to a multilayer thin emulsion film including a substrate, 1 to 100 layers of first composite thin films, and 1 to 100 layers of second composite thin films wherein the first composite thin films and the second composite thin films are laminated alternately with each other on the substrate, wherein each of the first composite thin films releases an active substance in a specific temperature range and consists of a cross-linkable cationic polymer layer coated on the substrate surface and a nanoemulsion layer including a plurality of nanoemulsions arrayed on the polymer layer, wherein each of the second composite thin films is disposed on the first composite thin film and consists of a cross-linkable cationic polymer layer coated on the surface of the first composite thin film and a nanofiber layer formed on the polymer layer, and wherein each of the nanoemulsions is a spherical particle consisting of (a) a core including the active substance and an oil and a shell including (b) an amphiphilic polymer consisting of a hydrophobic polymer and a hydrophilic polymer and (c) lecithin and continuously or discontinuously surrounding the core.

The substrate and the polymer layer are bound together by an attractive electrostatic force, the polymer layer and the nanoemulsion layer are bound together by an attractive electrostatic force, and the polymer layer and the nanofiber layer are bound together by an attractive electrostatic force. In the thin emulsion film of the present invention, the substrate is negatively charged by plasma treatment. In each of the first composite thin films, the polymer layer includes a positively charged polymer and the amphiphilic polymer and the lecithin constitute the surface of the nanoemulsion layer. In each of the second composite thin films, the polymer layer includes a positively charged polymer and the nanofiber layer includes nanofibers.

The substrate and the polymer layer are bound together by an attractive electrostatic force due to their opposite polarities. The polymer layer and the nanoemulsion layer are bound together by an attractive electrostatic force due to their opposite polarities. The polymer layer and the nanofiber layer are bound together by an attractive electrostatic force due to their opposite polarities. That is, the layer including the positively charged polymer is not bound to the layer including the nanoemulsions and the layer including the positively charged polymer is not bound to the layer including the nanofibers, but the polymer is directly bound to the nanoemulsions and the nanofibers.

The presence of the nanofiber layers allows extended release of the active substance and the oil in a specific temperature range. Specifically, the thin emulsion film including the nanofiber layers releases the active substance and the oil at a 1.5- to 2-fold lower rate than thin emulsion films without nanofiber layers.

The oil is not particularly limited so long as it is usually used in the preparation of oil-in-water nanoemulsions. For example, the oil may be selected from the group consisting of silicone emulsifiers, O/W emulsifiers, ester oils, silicone oils, hydrocarbon oils, waxes, natural oils, liquid animal and vegetable oils and fats, and mixtures thereof. None of these oils affect the release time and rate of the active substance, which was demonstrated through experiments.

Any amphiphilic block copolymer that can form oil-in-water nanoemulsions may be used without particular limitation. The amphiphilic block copolymer may be a polyethylene glycol (PEG)-polycaprolactone (PCL) copolymer having polycaprolactone (PCL) as a hydrophobic block and polyethylene glycol (PEG) as a hydrophilic block. The amphiphilic block copolymer may have a molecular weight ranging from 100 to 100,000 daltons and a degree of polymerization ranging from 1.0 to 1.5. Within these ranges, the amphiphilic block copolymer can be structurally controlled such that the active substance and the oil are slowly released in a desired temperature range (60-80° C.).

The polymer layer improves the durability of the nanoemulsions, making it easy to laminate a large amount of the nanoemulsions thereon. In addition, the polymer layer adheres well to the nanoemulsions, which is advantageous in preventing leakage or loss of the nanoemulsions.

The polycaprolactone and the polyethylene glycol are preferably present in a weight ratio of 1-1.5:1 in the amphiphilic block copolymer. Within this range, the chemical bonding between the polycaprolactone and the polyethylene glycol makes the nanoemulsions highly durable.

The nanoemulsions may have an average particle diameter of 0.1 to 100 μm. If the average particle diameter of the nanoemulsions is less than 0.1 μm, only very small amounts of the active substance and the oil are loaded into the cores. Meanwhile, if the average particle diameter of the nanoemulsions exceeds 100 μm, the durability of the nanoemulsions deteriorates considerably, with the result that the active substance and the oil are released even at low temperatures.

The amount of the oil loaded into the cores of the nanoemulsions is preferably from 1 to 10 parts by weight, based on 100 parts by weight of the nanoemulsions. The loading of the oil in an amount of less than 1 part by weight makes the role of the oil as a carrier meaningless. Meanwhile, the loading of the oil in an amount of more than 10 parts by weight leads to a reduction in the durability of the nanoemulsions, causing the nanoemulsions to collapse.

When the durability, average particle diameter, and preparation processes of the nanoemulsions are taken into consideration, as described above, it is preferred that the amount of the cores including the active substance and the oil is from 0.2 to 1.0 part by weight, based on 100 parts by weight of the thin emulsion film.

The positively charged polymer may be selected from the group consisting of polyallylamine hydrochloride, polyethyleneimine, polylysine, polydimethyldiallylammonium chloride, and chitosan. Polydimethyldiallylammonium chloride is most preferred.

The substrate may be negatively charged by plasma treatment, which enhances the adhesion of the substrate to the polymer layer.

Any active substance that is soluble in the oil and is applicable to skin, mucosa, scalp or hair may be used without particular limitation. Any active substance that can be used in a wide range of applications, for example, cosmetics, drugs, flavors and dyes, and is slowly released into a desired target at a specific temperature may be used.

The cosmetics may include basic cosmetic compositions selected from emulsions, emollients, lotions, creams, packs, gels, patches, and sprays (mists), color tone cosmetic compositions selected from lipsticks, makeup bases, and foundations, cleansers selected from shampoos, rinses, body cleansers, toothpastes, and mouthwashes, and hair cosmetics selected from hair conditioners such as hair tonics, gels, and mousses, hair restorers, and hair dyes. Drugs or quasi-drugs may be applied in the form of lotions, ointments, gels, creams, patches or sprays.

The nanofibers may have an average diameter in the range of 0.20 to 0.45 μm. Outside this range, the active substance and the oil are not released even when a specific temperature is reached.

The first composite thin films and the second composite thin films of the thin emulsion film are laminated alternately with each other. Each of the second composite thin film consists of the polymer layer and the nanofiber layer. Each of the first composite thin films consists of the polymer layer and the nanoemulsion layer. The polymer layer of the second composite thin film and the polymer layer of the first composite thin film may be composed of the same or different materials.

The nanofibers are preferably present in an amount of 1 to 10 parts by weight, based on 100 parts by weight of the nanofiber layers. If the amount of the nanofibers is less than 1 part by weight, the effect of improving the durability of the nanoemulsions is negligible. Meanwhile, if the amount of the nanofibers exceeds 10 parts by weight, the active substance and the oil are not released even when a specific temperature is reached and tend to discolor.

Another aspect of the present invention is directed to a method for preparing a multilayer thin emulsion film, including: I) mixing a dispersed phase solution with an aqueous suspension to prepare a mixture solution including nanoemulsions; II) treating the surface of a substrate with a plasma to negatively charge the substrate surface; III) immersing the substrate in a solution including a positively charged polymer to form a polymer layer; IV) withdrawing the substrate from the solution and immersing the withdrawn substrate in the mixture solution including nanoemulsions to form a nanoemulsion layer on the polymer layer; and V) repeating steps III) and IV) to form 1 to 100 layers of composite thin films.

Figure 3:
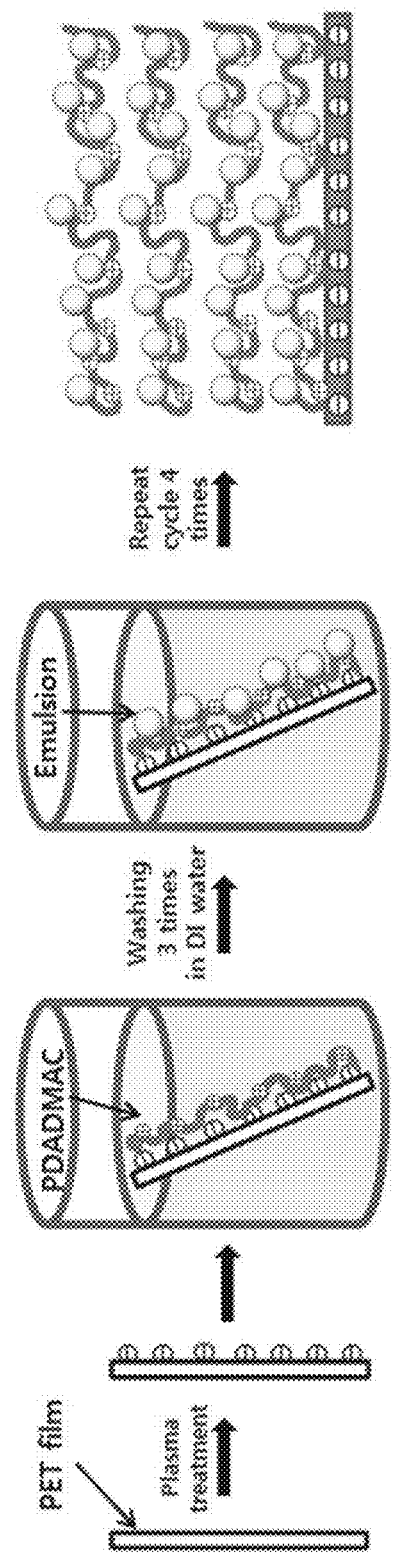
FIG. 3 shows a series of steps of a method for preparing a thin emulsion film according to the present invention.

FIG. 3 shows the steps of the method for preparing a thin emulsion film according to the present invention.

First, a dispersed phase solution is mixed with an aqueous medium to prepare a mixture solution including nanoemulsions (step I)). The dispersed phase solution includes (a) an amphiphilic polymer as a major stabilizer, (b) lecithin as an auxiliary surfactant, and (c) an oil. The amphiphilic polymer consists of poly-caprolactone as a hydrophobic polymer and polyethylene oxide as a hydrophilic polymer.

The dispersed phase solution dispersed in and mixed with the aqueous medium forms oil-in-water nanoemulsions.

That is, the nanoemulsions are formed by inducing effective self-assembly of the amphiphilic block copolymer at the oil/water interface using phase inversion emulsification and introducing highly biocompatible ionic lecithin as an auxiliary surfactant into the self-assembled amphiphilic block copolymer to form more rigid polymer-lecithin hybrid membranes at the oil/water interface of the emulsion.

Thereafter, the surface of a substrate is modified to negatively charge the substrate surface (step II)).

The substrate is negatively charged by exposure to a UV ozone lamp or treatment with an oxygen plasma. The method of the present invention uses an oxygen plasma to negatively charge the substrate surface.

The substrate can be made of a resin selected from the group consisting of polyethylene terephthalate, polyethylene naphthalate, acrylate resins, polyester, styrene resins, transparent teflon resins, polyimide resins, polyamide resins, polyesterimide resins, cellulose acylate resins, polyurethane, polyether ether ketone resins, polycarbonate resins, polyolefin resins, polyarylate resins, polyethersulfone, polysulfone, cycloolefin resins, and polyethylene resins.

The negatively charged substrate may be washed with DI water to remove impurities, etc.

In step III), the substrate is immersed in a solution including a positively charged polymer to form a polymer layer This immersion allows binding of the positively charged polymer to the substrate surface by an attractive electrostatic force. This simple immersion or dipping of the substrate makes the method of the present invention very simple and easy to carry out, contributing to cost reduction and time savings.

Step III) can be carried out for a sufficient time, preferably 1 to 20 minutes, such that the positively charged polymer is sufficiently bound to the substrate surface.

The solution including the positively charged polymer is not particularly limited so long as the positively charged polymer can be uniformly dispersed therein. The positively charged polymer is bound to the negatively charged substrate surface by an attractive electrostatic force to form a positively charged polymer layer.

The positively charged polymer can be selected from the group consisting of polyallylamine hydrochloride, polyethyleneimine, polylysine, polydimethyldiallylammonium chloride, and chitosan. Polydimethyldiallylammonium chloride is most preferred.

Thereafter, the substrate may be washed with deionized water to remove residual solution, impurities, etc.

Next, the substrate is withdrawn from the solution and is immersed in the mixture solution including nanoemulsions to form a nanoemulsion layer on the polymer layer (step IV)).

When the withdrawn substrate is immersed in the solution including negatively charged nanoemulsions, a nanoemulsion layer is formed on the polymer layer by an attractive electrostatic force.

The nanoemulsion layer formed on the polymer layer is composed of the amphiphilic block copolymer and the lecithin and has more rigid polymer-lecithin hybrid membranes at the oil/water interface.

The thickness of the nanoemulsion layer can be adjusted by controlling the average particle diameter of the nanoemulsions.

Step IV) can be carried out for 1 to 20 minutes.

After completion of step IV), the substrate may be washed with deionized water to remove impurities, residual solution, etc.

Steps III) and IV) are repeated several times (step V)) to form 1 to 100 layers of composite thin films. The number of the composite thin films can be determined depending on how many times steps III) and IV) are repeated.

After formation of the stable anionic nanoemulsions, steps III) and IV) are repeated (layer-by-layer assembly) to prepare a stable thin emulsion film in which 1 to 100 layers of composite thin films are laminated on the cationic polymer layer and the plasma-treated substrate.

When the thin emulsion film is heated above a predetermined temperature, the oil loaded into the thin nanoemulsion film and the polymer components surrounding the oil undergo phase separation by spinodal decomposition. As a result of phase separation, the oil and the active substance leak from the cores and are released from the thin emulsion film into a target.

Yet another aspect of the present invention is directed to a method for preparing a multilayer thin emulsion film, including: I) mixing a dispersed phase solution with an aqueous suspension to prepare a mixture solution including nanoemulsions; II) treating the surface of a substrate with a plasma to negatively charge the substrate surface; III) immersing the substrate in a solution including a positively charged polymer to form a polymer layer; IV) withdrawing the substrate from the solution and immersing the withdrawn substrate in the mixture solution including nanoemulsions to form a first composite thin film in which a nanoemulsion layer is formed on the polymer layer; V) withdrawing the substrate formed with the first composite thin film from the solution and immersing the withdrawn substrate in a solution including a positively charged polymer to form a polymer layer on the first composite thin film; and VI) withdrawing the substrate from the solution and immersing the withdrawn substrate in a mixture solution including nanofibers to form a second composite thin film in which a nanofiber layer is formed on the polymer layer.

First, a dispersed phase solution is mixed with an aqueous medium to prepare a mixture solution including nanoemulsions (step I)). The dispersed phase solution includes (a) an amphiphilic polymer as a major stabilizer, (b) lecithin as an auxiliary surfactant, and (c) an oil. The amphiphilic polymer consists of poly-caprolactone as a hydrophobic polymer and polyethylene oxide as a hydrophilic polymer.

The dispersed phase solution dispersed in and mixed with the aqueous medium forms oil-in-water nanoemulsions.

That is, the nanoemulsions are formed by inducing effective self-assembly of the amphiphilic block copolymer at the oil/water interface using phase inversion emulsification and introducing highly biocompatible ionic lecithin as an auxiliary surfactant into the self-assembled amphiphilic block copolymer to form more rigid polymer-lecithin hybrid membranes at the oil/water interface of the emulsion.

Thereafter, the surface of a substrate is modified to negatively charge the substrate surface (step II)).

The substrate is negatively charged by exposure to a UV ozone lamp or treatment with an oxygen plasma. The method of the present invention uses an oxygen plasma to negatively charge the substrate surface.

The substrate can be made of a resin selected from the group consisting of polyethylene terephthalate, polyethylene naphthalate, acrylate resins, polyester, styrene resins, transparent teflon resins, polyimide resins, polyamide resins, polyesterimide resins, cellulose acylate resins, polyurethane, polyether ether ketone resins, polycarbonate resins, polyolefin resins, polyarylate resins, polyethersulfone, polysulfone, cycloolefin resins, and polyethylene resins.

The negatively charged substrate may be washed with DI water to remove impurities, etc.

In step III), the substrate is immersed in a solution including a positively charged polymer to form a polymer layer This immersion allows binding of the positively charged polymer to the substrate surface by an attractive electrostatic force. This simple immersion or dipping of the substrate makes the method of the present invention very simple and easy to carry out, contributing to cost reduction and time savings.

Step III) can be carried out for a sufficient time, preferably 1 to 20 minutes, such that the positively charged polymer is sufficiently bound to the substrate surface.

The solution including the positively charged polymer is not particularly limited so long as the positively charged polymer can be uniformly dispersed therein. The positively charged polymer is bound to the negatively charged substrate surface by an attractive electrostatic force to form a positively charged polymer layer.

The positively charged polymer can be selected from the group consisting of polyallylamine hydrochloride, polyethyleneimine, polylysine, polydimethyldiallylammonium chloride, and chitosan. Polydimethyldiallylammonium chloride is most preferred.

Thereafter, the substrate may be washed with deionized water to remove residual solution, impurities, etc.

Next, the substrate is withdrawn from the solution and is immersed in the mixture solution including nanoemulsions to form a first composite thin film in which a nanoemulsion layer is formed on the polymer layer (step IV)).

When the withdrawn substrate is immersed in the solution including negatively charged nanoemulsions, a nanoemulsion layer is formed on the polymer layer by an attractive electrostatic force.

The nanoemulsion layer formed on the polymer layer is composed of the amphiphilic block copolymer and the lecithin and has more rigid polymer-lecithin hybrid membranes at the oil/water interface.

The thickness of the nanoemulsion layer can be adjusted by controlling the average particle diameter of the nanoemulsions.

Step IV) can be carried out for 1 to 20 minutes.

After completion of step IV), the substrate may be washed with deionized water to remove impurities, residual solution, etc.

In the resulting first composite thin film, the nanoemulsion layer is formed on the polymer layer.

The substrate formed with the first composite thin film is withdrawn from the solution and is immersed in a solution including a positively charged polymer to form a polymer layer on the first composite thin film (step V)).

Thereafter, the substrate is withdrawn from the solution and is immersed in a mixture solution including nanofibers to form a second composite thin film in which a nanofiber layer is formed on the polymer layer (step VI)).

When the withdrawn substrate is immersed in the solution including negatively charged nanofibers, a nanofiber layer is formed on the polymer layer by an attractive electrostatic force. In the resulting laminate structure, the second composite thin film consists of the polymer layer and the nanofiber layer and is laminated on the first composite thin film.

The nanofibers are preferably cellulose nanofibers and may have an average diameter of 0.20 to 0.45 μm.

The nanofiber layer enhances the mechanical properties of the final thin emulsion film and allows controlled release of the oil and the active substance from the cores. Preferably, the nanofiber layer has a structure in which cellulose nanofibers are laminated on the nanoemulsion layer and the polymer layer.

The thin emulsion film delays the release of the oil and the active substance by at least 1.5 to 2-fold due to its enhanced surface characteristics.

The solution including nanofibers may have a concentration of 0.1 to 5 wt %. If the concentration of the solution is lower than 0.1 wt %, the nanofibers do not cover the entire surface of the underlying polymer layer. Meanwhile, if the concentration of the solution is higher than 5 wt %, the nanofibers aggregate in the inorganic solution. This aggregation prevents uniform dispersion of the nanofibers in the solution and impedes the release of the oil from the thin emulsion film.

The method may further include VII) repeating steps III) to VI) several times to form a 1- to 100-layer composite thin film. The number of layers of the composite thin film can be determined depending on how many times steps III) and VI) are repeated. For example, the 2-layer composite thin film may have a first composite thin film/second composite thin film/first composite thin film/second composite thin film structure.

Specifically, the composite thin film may have a polymer layer/nanoemulsion layer/polymer layer/nanofiber layer/polymer layer/nanoemulsion layer . . . structure.

After formation of the stable anionic nanoemulsions, steps III) and VI) are repeated (layer-by-layer assembly) to prepare a stable thin emulsion film in which 1 to 100 layers of first composite thin films and 1 to 100 layers of second composite thin films are laminated on the cationic polymer layer and the plasma-treated substrate.

Spinodal decomposition of the multilayer thin emulsion film is induced, with the result that the oil leaks or is released from the emulsions. This oil leakage causes a change in surface characteristics. The thin emulsion film has the function of releasing the active substance and the oil into a target at a specific temperature. Therefore, the multilayer thin emulsion film is expected to be useful as a smart drug release material in a variety of applications, including cosmetics, pharmaceuticals, and biotherapy.

The present invention will be explained in more detail with reference to the following examples. It will be evident to those skilled in the art that these examples are not intended to limit the scope of the invention and various modifications and changes can be made thereto without departing from the scope and spirit of the invention.

Examples 1 and 2: Preparation of Nanoemulsions

Poly(ethylene oxide)-b-poly(ε-caprolactone) (PEO-b-PCL) (PCL:PEO=1.07:1, molecular weight=7.3 kDa, polydispersity index=1.37) consisting of a hydrophobic polymer (PCL) and a hydrophilic polymer (PEO) was prepared. The block copolymer and lecithin (Lipoid S75-3) were completely dissolved in tetrahydrofuran (THF) to prepare a dispersed phase. Then, an oil was added to the dispersed phase.

Here, the block copolymer PEO-b-PCL and the lecithin were used in a total amount of 1 to 10 parts by weight, based on 100 parts by weight of the dispersed phase. The average particle diameter of final nanoemulsions was dependent on the total amount of the block copolymer and the lecithin. When the total amount of the block copolymer and the lecithin was 1 part by weight, nanoemulsions having an average particle diameter of 30 nm were obtained (Example 1). When the total amount of the block copolymer and the lecithin was 10 parts by weight, nanoemulsions having an average particle diameter of 200 nm were obtained (Example 2). The specific amounts of the block copolymer, the lecithin, the oil, and the solvent are shown in Table 1.

In Examples 1 and 2, the total amounts of the block copolymer PEO-b-PCL and the lecithin were set to 1 and 10 parts by weight, based on 100 parts by weight of the dispersed phase, respectively.

Next, Nile red was added to the dispersed phase to discern nanoemulsions by optical or fluorescence microscopy. The oily dispersed phase was slowly added to distilled water at a rate of 100 l/min to prepare an oil-in-water (o/w) emulsion.

The emulsion was distilled under reduced pressure to remove remaining THF. Thereafter, the size of the emulsion drops was controlled by irradiation with ultrasonic waves from a probe-type sonicator (VCX130, Sonic & Materials Inc., USA) for 5 min, completing the preparation of nanoemulsions. The average particle diameter of the nanoemulsions was measured by dynamic light scattering using an electron transmission microscope (TEM, LIPRA120, Carl Zeiss) and a particle size analyzer (ELS-Z2, Otsuka, Japan). The amount of surface charges was measured using a zeta potential-particle size analyzer (ELS-Z2, Otsuka, Japan). The emulsion was measured to have a surface potential of about −16 mV.

The oil was olive oil as a vegetable oil. Alternatively, any oil (such as a mineral oil or a drug-containing oil) other than olive oil may be used because the emulsifying capacity and the surface charges of the particles are determined only by the characteristics of the polymer.

The particle diameter can be controlled by the ratio of the polymer to the lecithin and the amount of the oil. In these examples, the amount of the oil was adjusted to control the particle diameter. Specifically, when the amount of the oil was 3 wt % with respect to the total weight of the emulsion, the average particle diameter was 100 nm. When the amount of the oil was 10 wt % with respect to the total weight of the emulsion, the average particle diameter was 20 nm.

TABLE 1

|  | PEO-b-PCL | Lecithin | Oil | Solvent |
|---|---|---|---|---|
| Example 1 | 5 | 1 | 3 | 91 |
| Example 2 | 5 | 1 | 10 | 84 |

Examples 3-6: Preparation of Thin Emulsion Films Consisting of Composite Thin Films Composed of Nanoemulsions and Cationic Polymer In these examples, thin emulsion films were prepared using an aqueous solution including 0.5 wt % of poly(diallyldimethylammonium chloride) (PDADMAC) and the aqueous nanoemulsion solution prepared in Example 1.

First, the surface of a PET film was modified by plasma treatment to make the surface of the PET film hydrophilic. The surface-modified PET film was alternately immersed in an aqueous solution including 0.5 wt % of poly(diallyldimethylammonium chloride) (PDADMAC) and the aqueous nanoemulsion solution prepared in Example 1 ("layer-by-layer assembly") to prepare a thin emulsion film in which polymer layers and nanoemulsion layers were laminated alternately with each other. The entire procedure was performed at room temperature.

When the procedure was performed once, a 1-layer composite thin film consisting of one polymer layer and one nanoemulsion layer was formed (Example 3). When the procedure was repeated 5, 10, and 20 times, 5-layer (Example 4), 10-layer (Example 5), and 20-layer (Example 6) composite thin films were formed, respectively.

The surface characteristics and thicknesses of the thin emulsion films were analyzed using an atomic force microscope (AFM, XE-100, Park system) operated in a non-contact tapping mode. To this end, the surface shape and roughness of each thin emulsion film were observed. AFM line data for the different cross-sectional heights of the thin emulsion films were analyzed. The thickness of the thin emulsion film increased with increasing number of layers (see FIG. 2).

0.26 parts by weight of the oil were observed to be present in 100 parts by weight of each of the thin emulsion films of Examples 3-6, which were prepared using the nanoemulsions prepared from the dispersed phase solution including 3 parts by weight of the oil with respect to 100 parts by weight of the solution in Example 1.

Examples 7-10: Preparation of Thin Emulsion Films Consisting of Composite Thin Films Composed of Nanoemulsions and Cationic Polymer Thin emulsion films were prepared in the same manner as in Examples 3-6, except that the nanoemulsions prepared in Example 2 were used instead of the nanoemulsions prepared in Example 1. Specifically, the thin emulsion films of Examples 7-10 consisted of 1 layer, 5 layers, 10 layers, and 20 layers of composite thin films, respectively.

0.86 parts by weight of the oil were observed to be present in 100 parts by weight of each of the thin emulsion films of Examples 7-10.

Examples 11-13: Preparation of Thin Emulsion Films Consisting of Composite Thin Films Composed of Nanoemulsions and Cationic Polymer Nanoemulsions including different amounts of an oil were prepared in the same manner as in Example 1.

First, the surface of a PET film was modified by plasma treatment to make the surface of the PET film hydrophilic. The surface-modified PET film was sequentially immersed in an aqueous solution including 0.5 wt % of poly(diallyldimethylammonium chloride) (PDADMAC), the aqueous nanoemulsion solution prepared in Example 1 or 2, an aqueous solution including 0.5 wt % of poly(diallyldimethylammonium chloride) (PDADMAC), and an aqueous solution of 1 wt % of anionic cellulose nanofibers to prepare a thin emulsion film in which the polymer layer, the nanoemulsion layer, the polymer layer, and the nanofiber layer were sequentially formed on the substrate (Example 11). The immersion process was repeated to prepare a thin emulsion film in which 5 layers of composite thin films were formed (Example 12) and a thin emulsion film in which 10 layers of composite thin films were formed (Example 13). The entire procedure was performed at room temperature.

The surface characteristics of the thin emulsion films were measured using a scanning electron microscope.

Examples 14-16: Preparation of Thin Emulsion Films Consisting of Composite Thin Films Composed of Nanoemulsions and Nanofibers Thin emulsion films were prepared in the same manner as in Examples 11-13, except that the nanoemulsions prepared in Example 2 were used instead of the nanoemulsions prepared in Example 1. Specifically, the thin emulsion films of Examples 14-16 consisted of 1 layer, 5 layers, and 10 layers of composite thin films, respectively.

Example 17: Preparation of Thin Emulsion Film Loaded with Retinol as Active Substance 1) Nanoemulsions Nanoemulsions were prepared in the same manner as in Example 2, except that 0.3 parts by weight of retinol with respect to 100 parts by weight of the dispersed phase were dissolved in the oil.

TABLE 2

| | PEO-b-PCL | Lecithin | Oil | Retinol (active substance) | Solvent |
|---|---|---|---|---|---|
| Example 17 | 5 | 1 | 10 | 0.3 | 83.7 |

2) Thin Emulsion Film

A thin emulsion film was prepared in the same manner as in Example 7, except that the nanoemulsions prepared in 1) of Example 17 were used instead of the nanoemulsions prepared in Example 2.

Example 18: Preparation of Thin Emulsion Film Loaded with Pyrene as Active Substance A thin emulsion film was prepared using a difficult-to-emulsify active substance and its function of slowly releasing the active substance at a specific temperature was confirmed by comparison with the function of the thin emulsion film using retinol as an active substance. For this purpose, hydrophobic luminescent pyrene was used as the active substance.

1) Nanoemulsions

Nanoemulsions were prepared in the same manner as in Example 2, except that 0.3 parts by weight of pyrene (Aldrich) with respect to 100 parts by weight of the dispersed phase were dissolved in the oil.

2) Thin Emulsion Film

A thin emulsion film (5-layer) was prepared in the same manner as in Example 8, except that the nanoemulsions prepared in 1) of Example 18 were used instead of the nanoemulsions prepared in Example 2.

Figure 2:
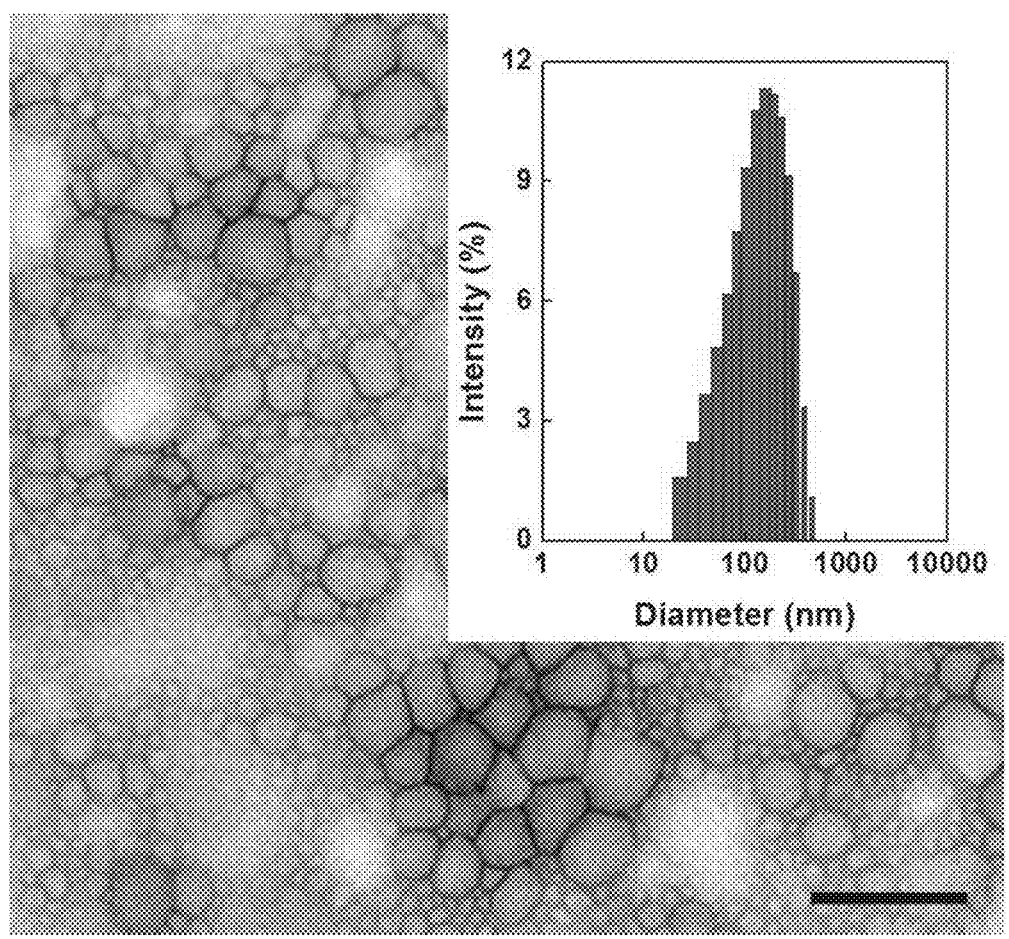
FIG. 2 is a transmission electron microscopy image of a thin emulsion film prepared in Example 6.

FIG. 2 is a transmission electron microscopy image of the thin emulsion film prepared in Example 6. The top right graph of FIG. 2 shows the average particle diameter distributions of the nanoemulsions with increasing number of layers of the composite thin films of the thin emulsion films prepared in Examples 3-6, which were measured by analyzing AFM line data for the different cross-sectional heights of the thin emulsion films using an atomic force microscope.

These results demonstrate that the nanoemulsions of Example 1 were aligned on the substrate, as explained above. The loaded oil (drug) was slowly released from the nanoemulsions directly formed into thin films on the substrate in a specific temperature range. This functional effect was not observed in the nanoemulsions before film formation.

Furthermore, the thin nanoemulsion films were loaded with larger amounts of the drug than the same amount of the nanoemulsions dispersed in the solution. Specifically, 0.86 or 0.26 parts by weight of the drug were present in 100 parts by weight of the thin emulsion film.

Figure 4:
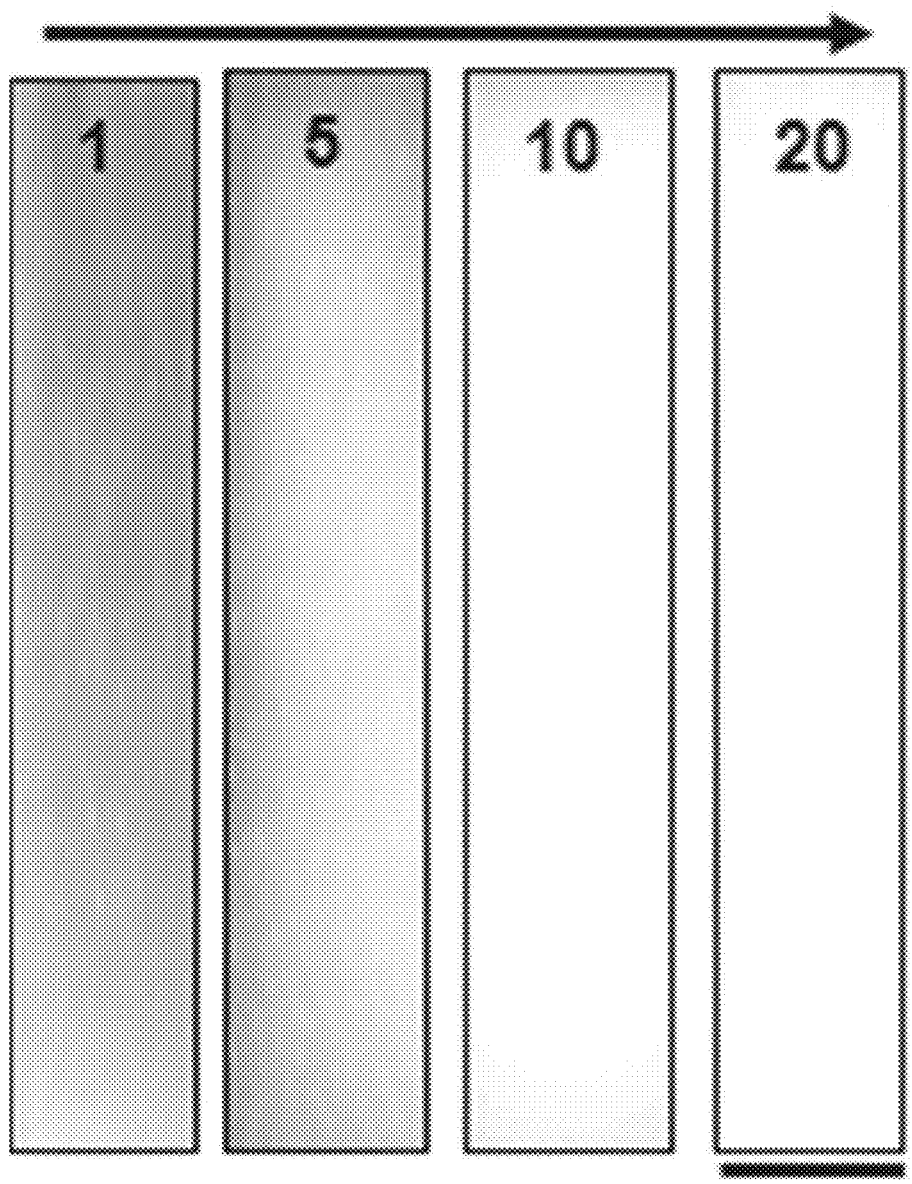
FIG. 4 shows actual surface shapes of thin emulsion films prepared in Examples 7-10.

FIG. 4 shows actual surface shapes of the thin emulsion films prepared in Examples 7-10. The surface color of the thin emulsion film became gradually bright with increasing number of the composite thin films. That is, the number of layers of the composite thin films, each of which consisted of the polymer layer and the nanoemulsion layer, was from 1 to 20 depending on how many times layer-by-layer assembly was repeated.

Figure 5A:
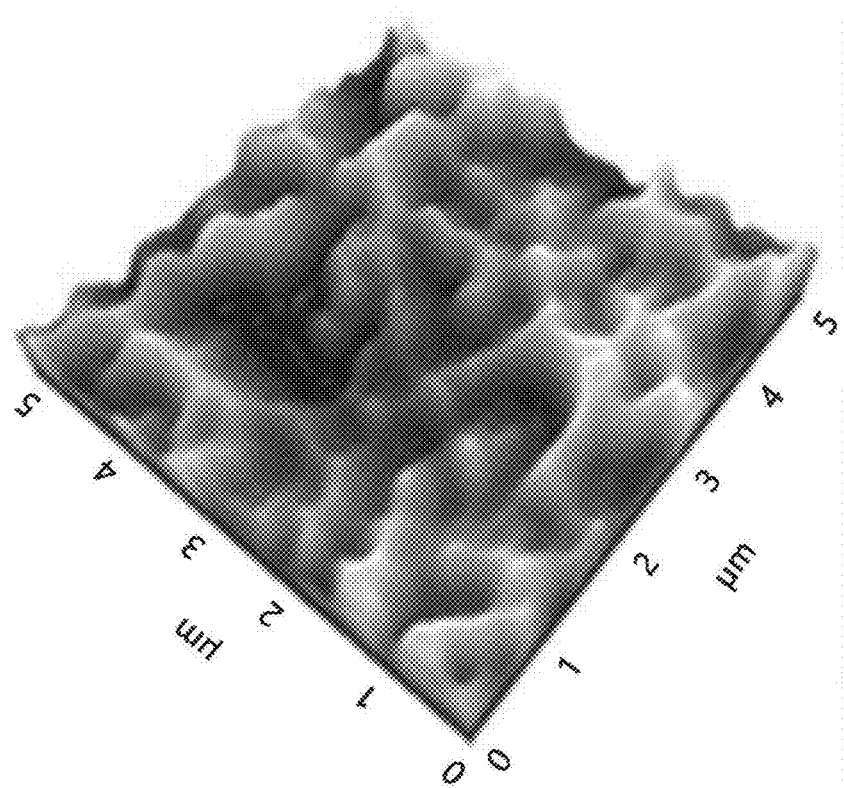
FIGS. 5*a* and 5*b* are atomic force microscopy images of a thin emulsion film prepared in Example 4.
Figure 5B:
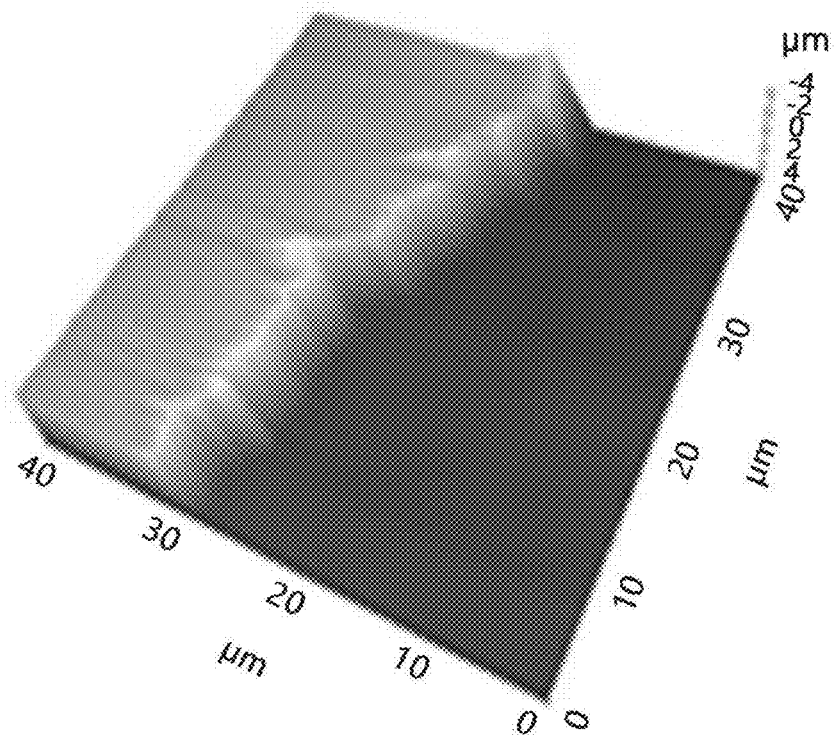
Figure 5C:
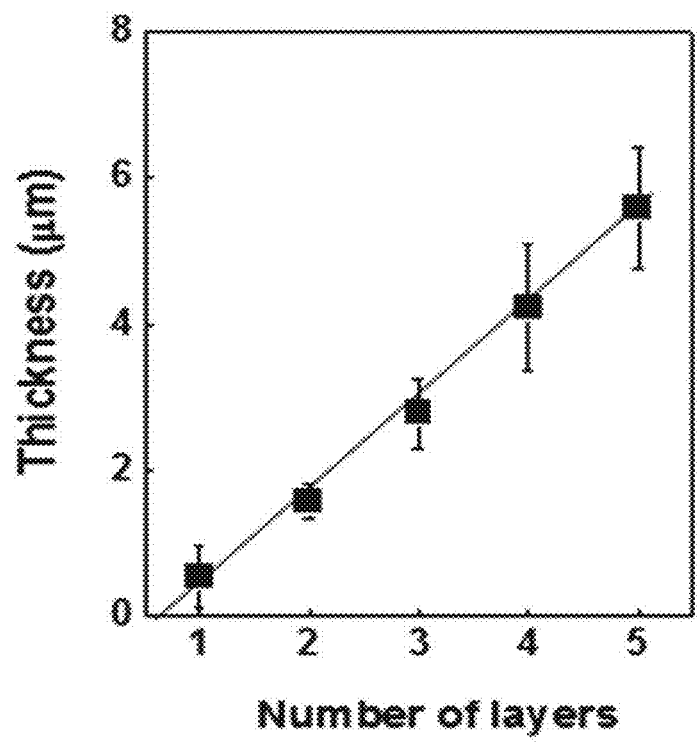
FIG. 5*c* shows a change in the thickness of a thin emulsion film prepared in Example 4 with increasing number of layers.

FIGS. 5a and 5b are atomic force microscopy images of the thin emulsion film prepared in Example 4. FIG. 5c shows a change in the thickness of the thin emulsion film prepared in Example 4 with increasing number of layers. As can be seen from these observations, the nanoemulsions were uniformly captured in the composite thin films of the thin emulsion film. The layer thicknesses were uniform (~1 μm each).

Figure 6:
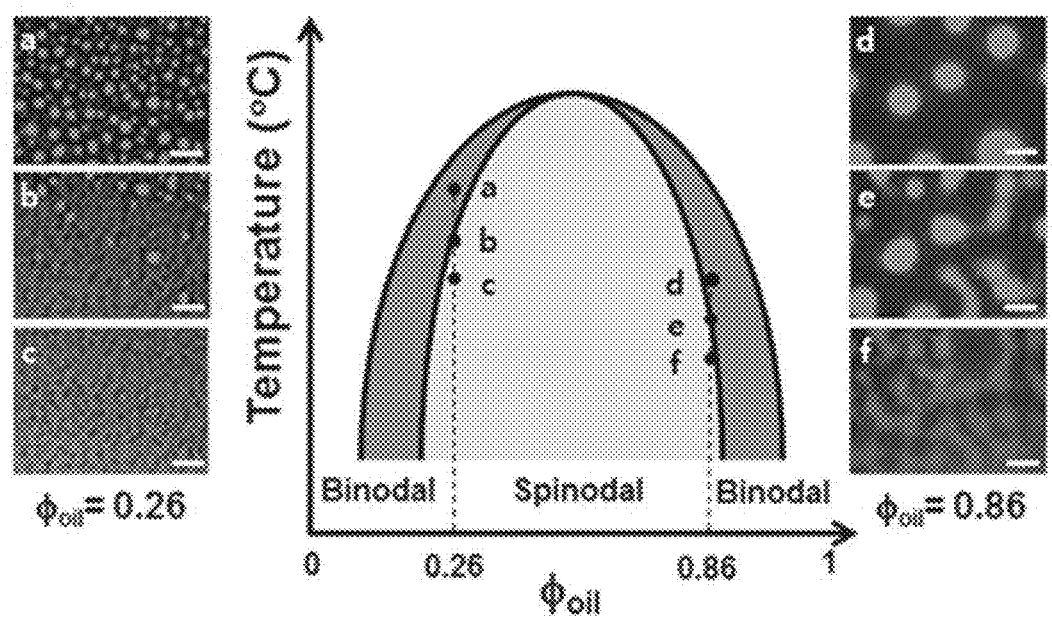
FIG. 6 graphically shows the behaviors of nanoemulsions in thin emulsion films prepared in Examples 3-7 at different temperatures and fluorescence microscopy images of the thin emulsion films.

FIG. 6 graphically shows the behaviors of the nanoemulsions in the thin emulsion films prepared in Examples 3-7 at different temperatures and fluorescence microscopy images of the thin emulsion films. Changes in the behavior and shape of the thin emulsion films prepared in Examples 3-7 during heating from 40° C. to 80° C. were analyzed by fluorescence microscopy.

The thin emulsion film prepared in Example 3 underwent phase separation by spinodal decomposition from 75° C., and as a result, its shape began to change (a of FIG. 6). The nanoemulsions coalesced at 80° C. to form several oil domains (b of FIG. 6) and the domains grew at 90° C. (c of FIG. 6).

The thin emulsion film prepared in Example 7 underwent phase separation by spinodal decomposition from 65° C., and as a result, its shape began to change (d of FIG. 6). Domains began to form at 70° C. (e of FIG. 6) and grew at 75° C. (f of FIG. 6).

The experimental results concluded that the thin emulsion films release the oil at different temperatures depending on the amount (parts by weight) of the oil irrespective of the number of layers of the composite thin films and the temperature ranges for oil release can be controlled depending on the weight of the oil loaded into the thin emulsion films.

Figure 7:
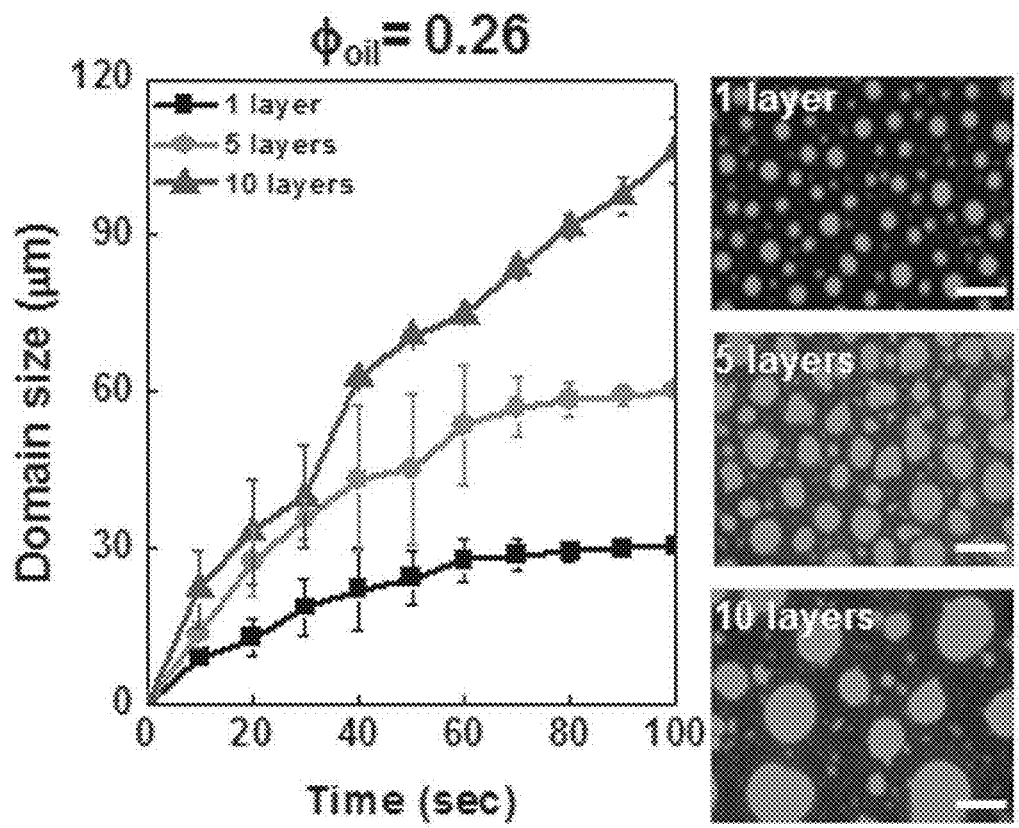
FIG. 7 shows the sizes of domains in thin emulsion films prepared in Examples 3-5, which were measured at different time points at a high temperature (60° C.)
Figure 8:
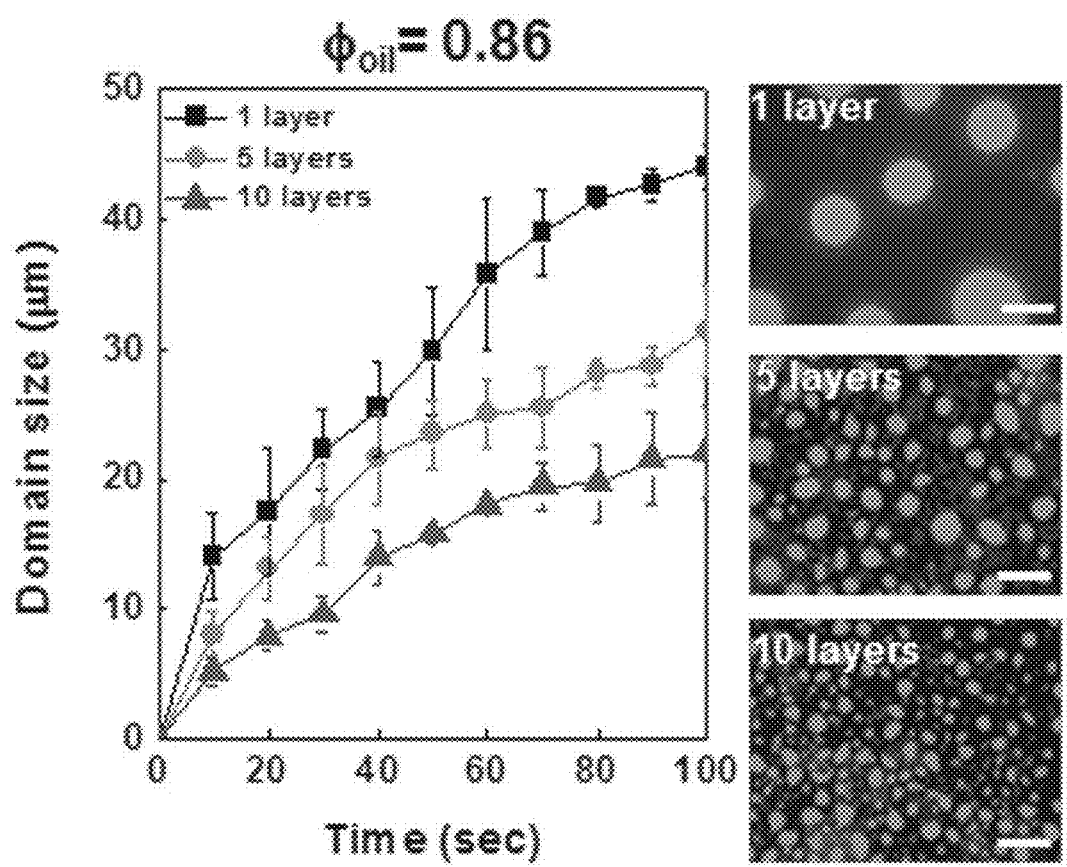
FIG. 8 shows the sizes of domains in thin emulsion films prepared in Examples 7-9, which were measured at different time points at a high temperature (60° C.). Scale bars indicate 50 µm.

FIG. 7 shows the sizes of domains in the thin emulsion films prepared in Examples 3-5, which were measured at different time points at a high temperature (60° C.). FIG. 8 shows the sizes of domains in the thin emulsion films prepared in Examples 7-9, which were measured at different time points at a high temperature (60° C.). Scale bars in FIG. 8 indicate 50 μm.

As shown in FIG. 7, the final domain size in the thin emulsion film of Example 3 including the 1-layer composite thin film consisting of the polymer layer and the nanoemulsion layer was 20 μm, the final domain size in the thin emulsion film of Example 4 including the 5 layers of composite thin films was 50 μm, and the final domain size in the thin emulsion film of Example 5 including the 10 layers of composite thin films was 100 μm. That is, the domain size increased in proportion to the number of the composite thin films.

As shown in FIG. 8, the final domain size in the thin emulsion film of Example 7 including the 1-layer composite thin film consisting of the polymer layer and the nanoemulsion layer was 40 μm, the final domain size in the thin emulsion film of Example 8 including the 5 layers of composite thin films was 30 μm, and the final domain size in the thin emulsion film of Example 9 including the 10 layers of composite thin films was 20 m. That is, when the nanoemulsions loaded with the excess oil were formed into thin films, the domain size decreased with increasing number of layers.

Figure 9A:
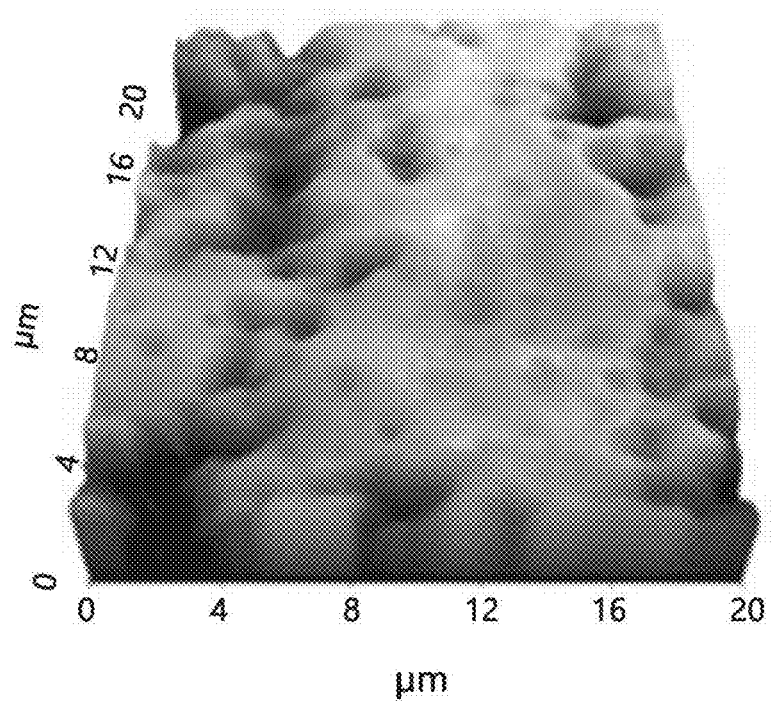
FIGS. 9*a* and 9*b* are images showing the surface of a thin emulsion film prepared in Example 8 before heating to 80° C., which were taken with an electrostatic force microscope (EFM, XE-100, Park system)
Figure 9B:
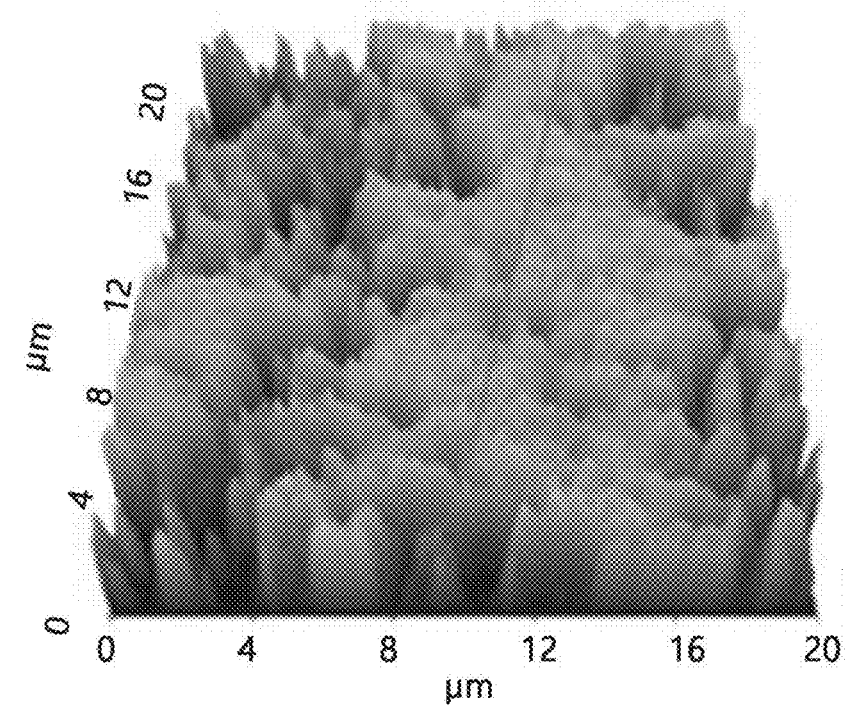
Figure 9C:
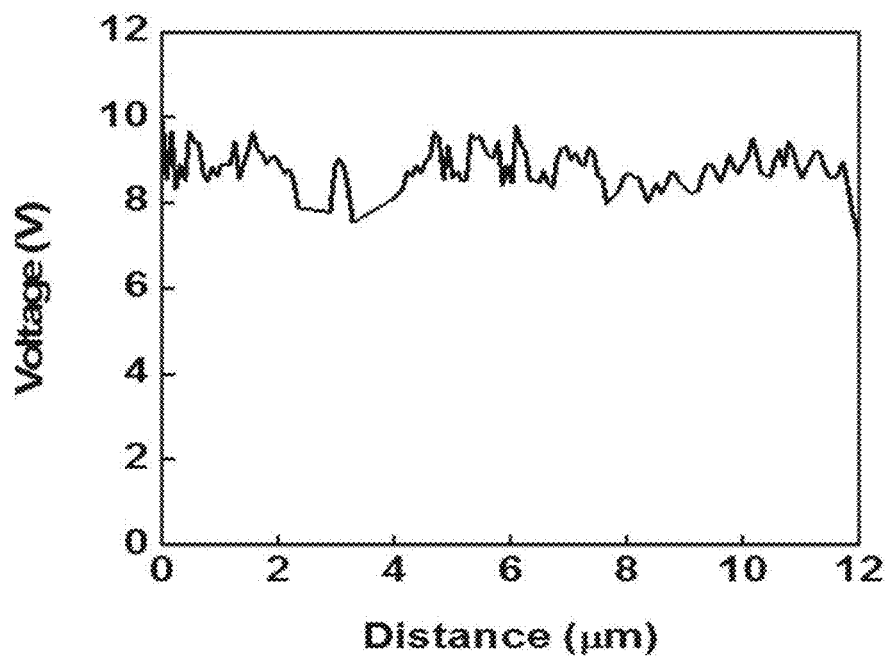
FIG. 9*c* shows the amount of surface charges on a thin emulsion film prepared in Example 8 before heating to 80° C.

FIGS. 9a and 9b are images showing the surfaces of the thin emulsion film prepared in Example 8 before heating to 80° C., which were taken with an electrostatic force microscope (EFM, XE-100, Park system). FIG. 9c shows the amount of surface charges on the thin emulsion film prepared in Example 8 before heating to 80° C.

Figure 9D:
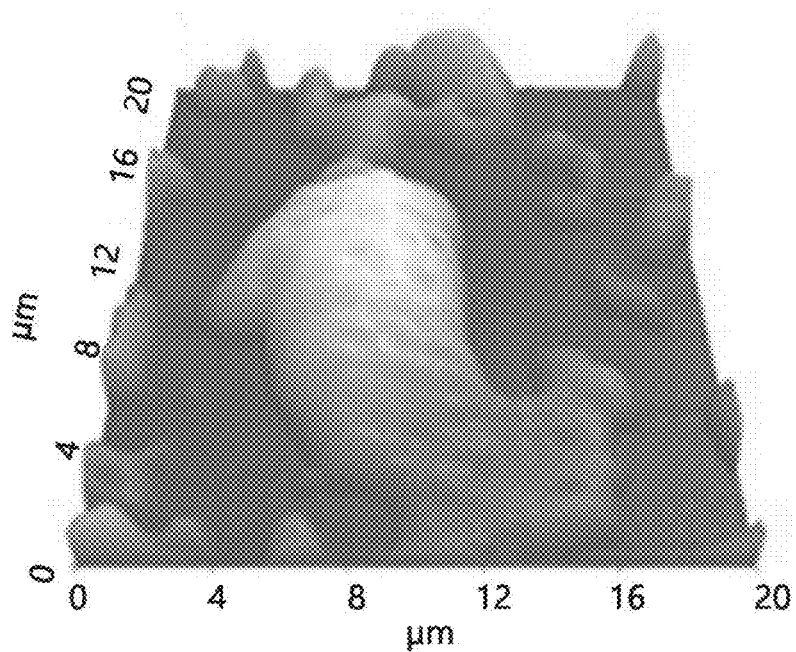
FIGS. 9*d* and 9*e* are images showing the surface of a thin emulsion film prepared in Example 8 before heating to 65° C., which were taken with an electrostatic force microscope (EFM, XE-100, Park system)
Figure 9E:
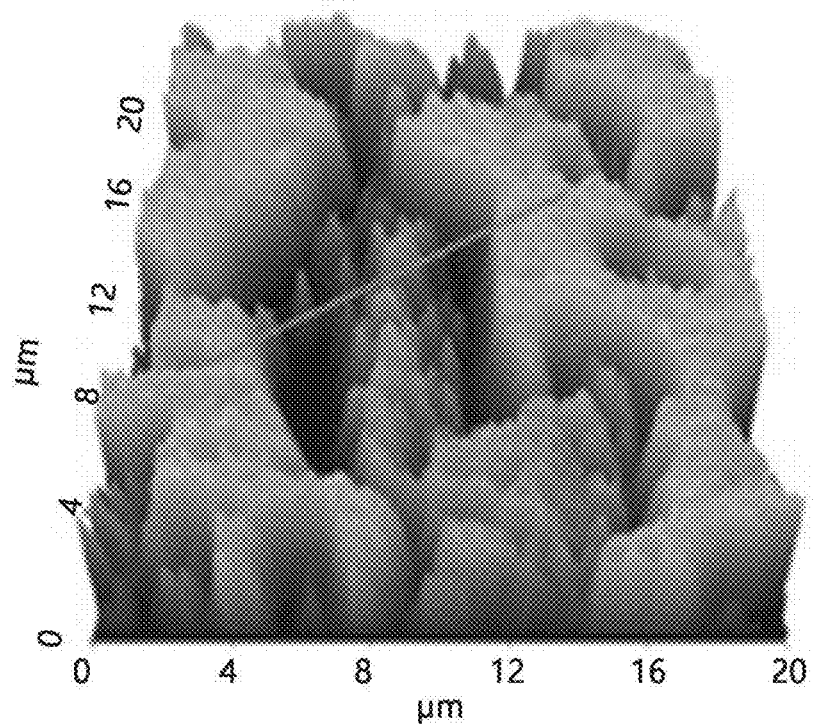
Figure 9F:
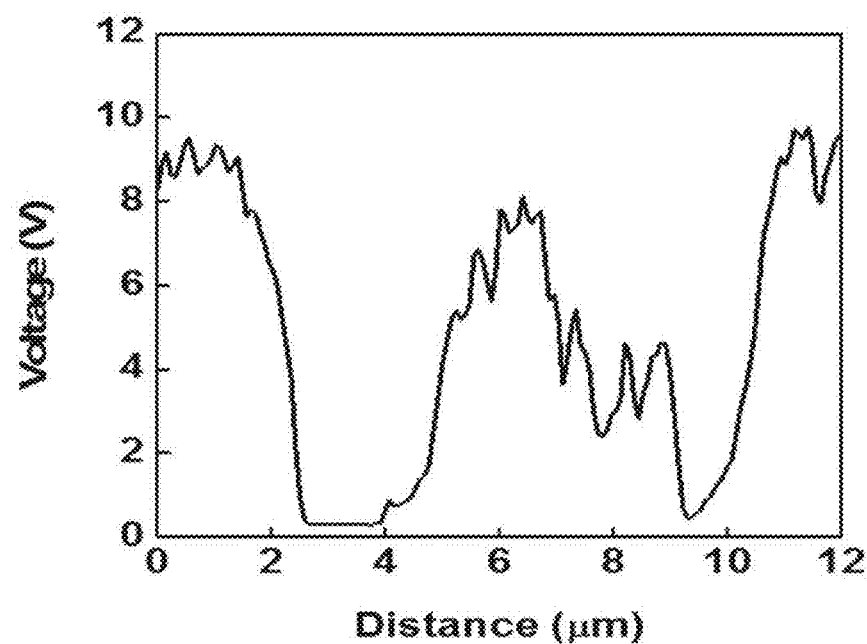
FIG. 9*f* shows the amount of surface charges on a thin emulsion film prepared in Example 8 before heating to 65° C.

FIGS. 9d and 9e are images showing the surface of the thin emulsion film prepared in Example 8 before heating to 65° C., which were taken with an electrostatic force microscope (EFM, XE-100, Park system). FIG. 9f shows the amount of surface charges on the thin emulsion film prepared in Example 8 before heating to 65° C.

Before heating, the surface of the thin emulsion film was even and the amount of surface charges on the thin emulsion film was 8-10 V, as shown in FIGS. 9a to 9f.

After heating to 65° C., the surface roughness of the thin emulsion film was increased and few or no surface charges was observed. The reason why the amount of surface charges was zero (0) is believed to be because the oil loaded into the nanoemulsions leaked and coalesced, and as a result, no current was passed through the coalesced portions.

In other words, when the thin emulsion film is placed under heat or specified temperature conditions, the oil loaded into the nanoemulsions leaks and coalesces, and as a result, the coalesced portions will become more hydrophobic, resulting in an increase in contact angle. This was validated through the following experiments.

Figure 10:
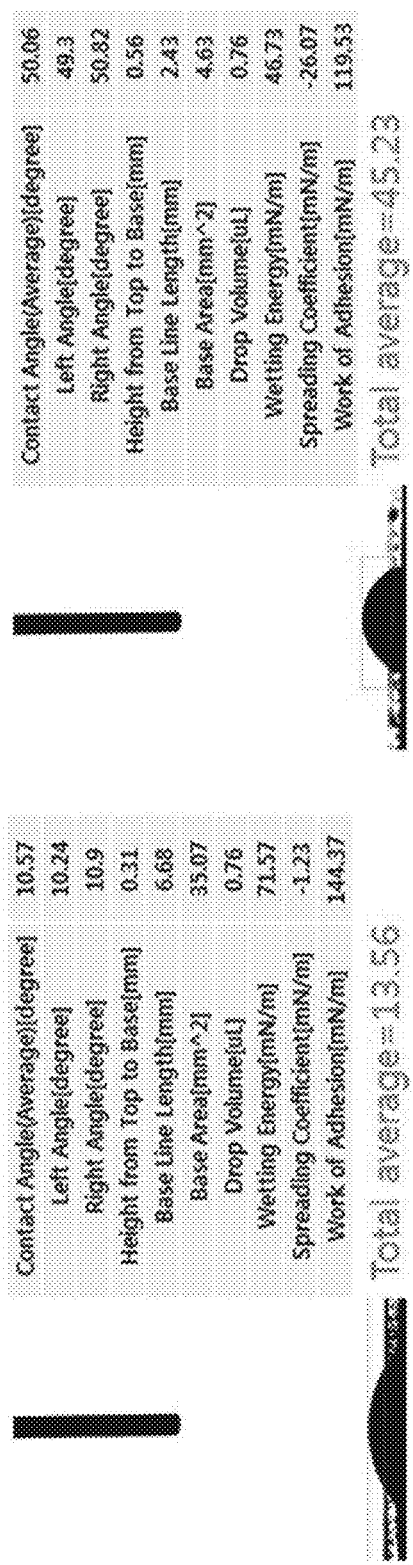
FIG. 10 shows contact angles on the surface of a thin emulsion film prepared in Example 8 (A) before and (B) after heating (60° C.)

FIG. 10 shows contact angles on the surface of the thin emulsion film prepared in Example 8 (A) before and (B) after heating (60° C.). The average contact angles of the thin emulsion film including the 5 layers of composite thin films before and after heating were observed to be 13.560 and 45.23°, respectively.

Figure 11:
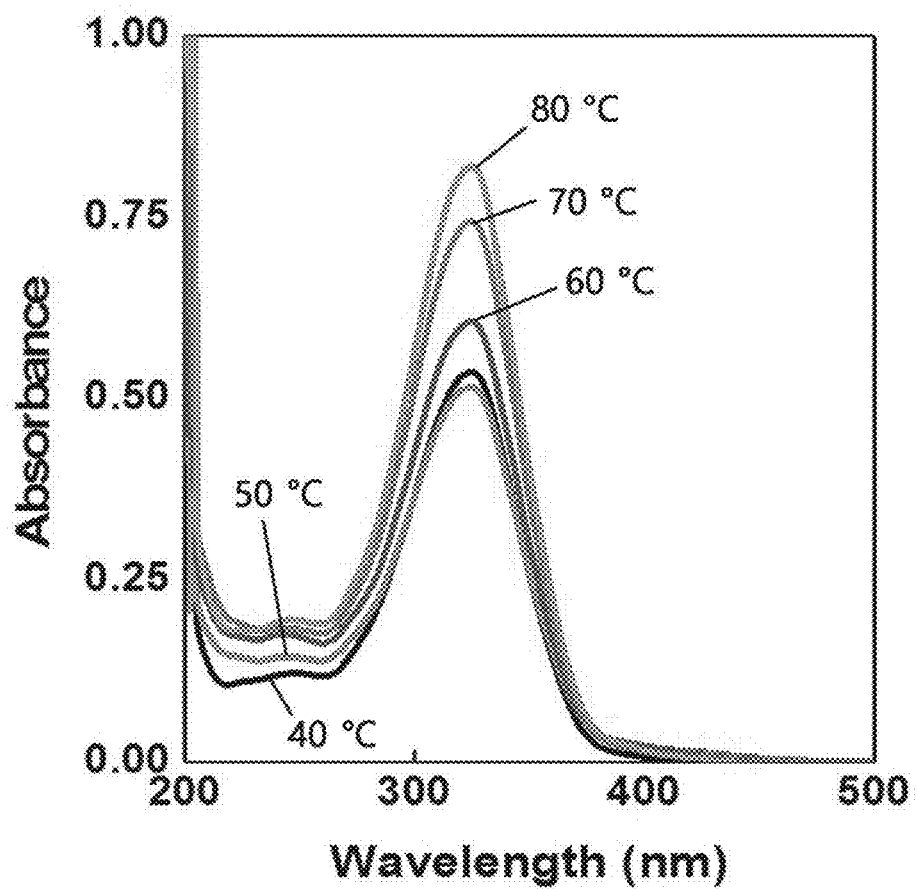
FIG. 11 shows UV-Vis spectra after heating of a thin emulsion film prepared in Example 17 loaded with retinol as an active substance at a rate of 10° C. from 40° C. to 80° C., immersion of the thin emulsion film in 8 ml of ethanol for 5 min, and collection of 3 ml of the ethanol.

FIG. 11 shows UV-Vis spectra after heating of the thin emulsion film prepared in Example 17 loaded with retinol as an active substance at a rate of 10° C. from 40° C. to 80° C., immersion of the thin emulsion film in 8 ml of ethanol for 5 min, and collection of 3 ml of the ethanol.

Figure 12:
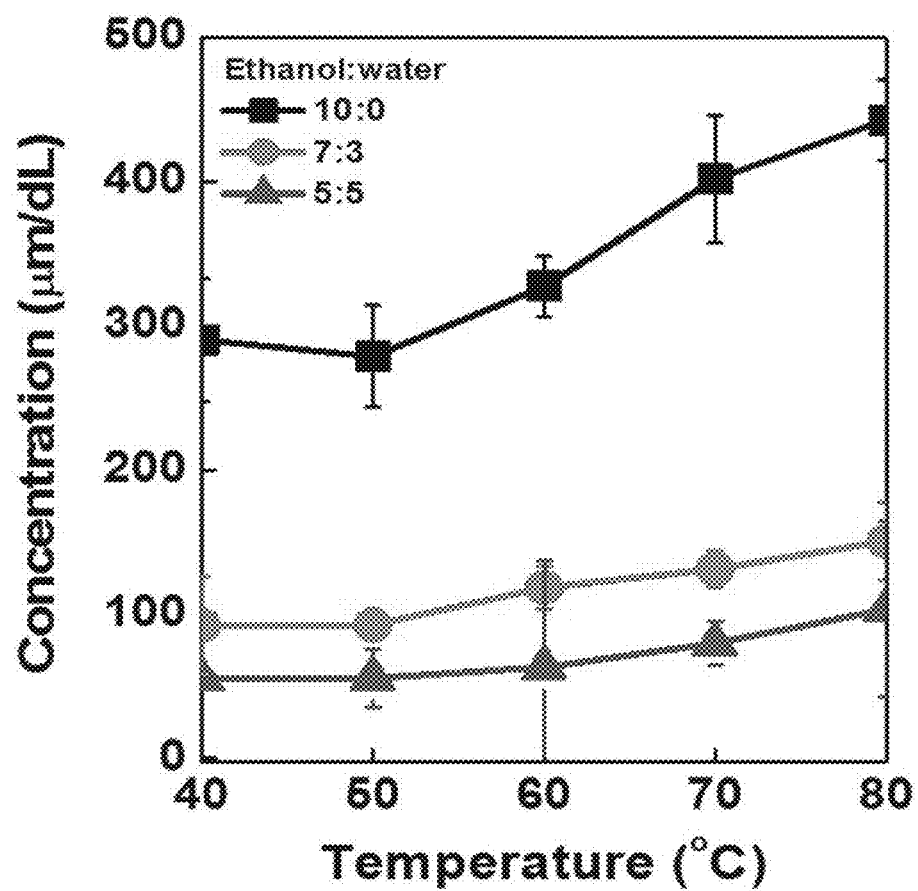
FIG. 12 shows the concentrations of retinol as an active substance after heating of a retinol-loaded thin emulsion film prepared in Example 17 at a rate of 10° C. from 40° C. to 80° C., immersion of the thin emulsion film in mixture solutions of ethanol and water in different ratios (10:0, 7:3, and 5:5) for 5 min, and collection of 3 ml of each of the mixture solutions.

FIG. 12 shows the concentrations of retinol as an active substance after heating of the retinol-loaded thin emulsion film prepared in Example 17 at a rate of 10° C. from 40° C. to 80° C., immersion of the thin emulsion film in mixture solutions of ethanol and water in different ratios (10:0, 7:3, and 5:5) for 5 min, and collection of 3 ml of each of the mixture solutions.

The release degrees of retinol from the thin emulsion film after heating to various temperatures were compared. Referring to FIGS. 11 and 12, only very small amounts of retinol remaining on the surface of the thin emulsion film were measured when heated to 40° C. and 50° C. Phase separation in the nanoemulsions of the thin emulsion film began to occur at 60° C., leading to a marked increase in the amount of retinol released. The amount of retinol released increased with increasing temperature.

Referring to FIG. 12, since retinol is soluble only in ethanol, the concentrations of retinol were measured by UV-Vis spectroscopy only when ethanol was used. When the aqueous ethanolic solutions were used, retinol was not substantially detected by UV-Vis spectroscopy. The reliability of the analysis results shown in FIGS. 11 and 12 could be confirmed.

Figure 13A:
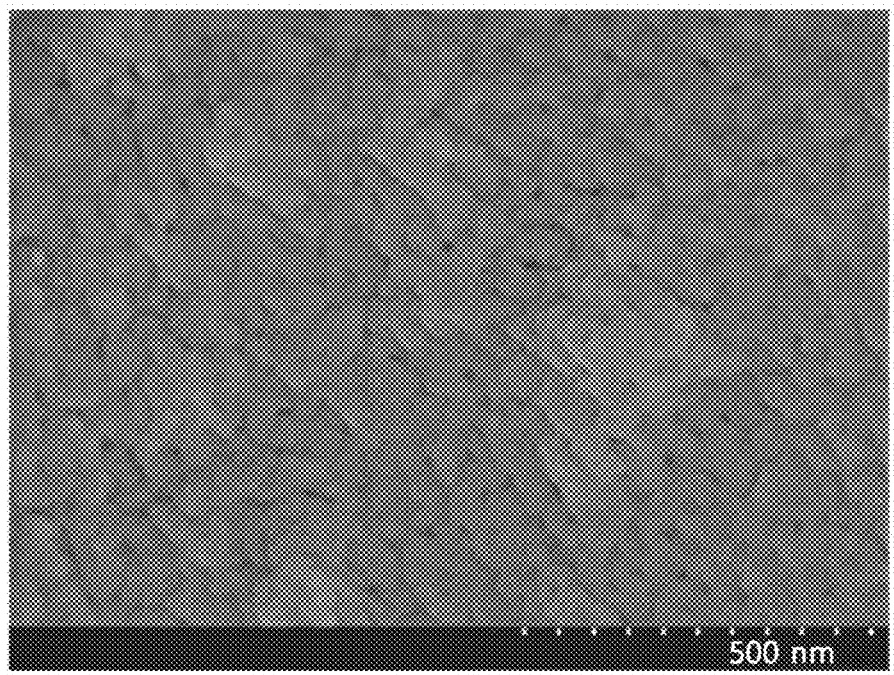
FIGS. 13a to 13c are scanning electron microscopy images of thin emulsion films prepared in Examples 14-16 after heating to 65° C., respectively.
Figure 13B:
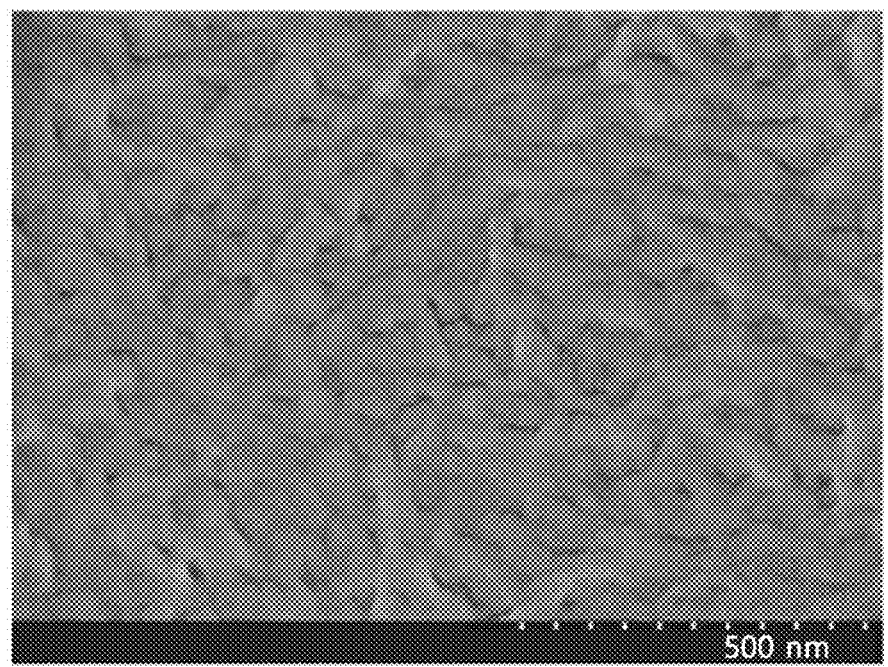
Figure 13C:
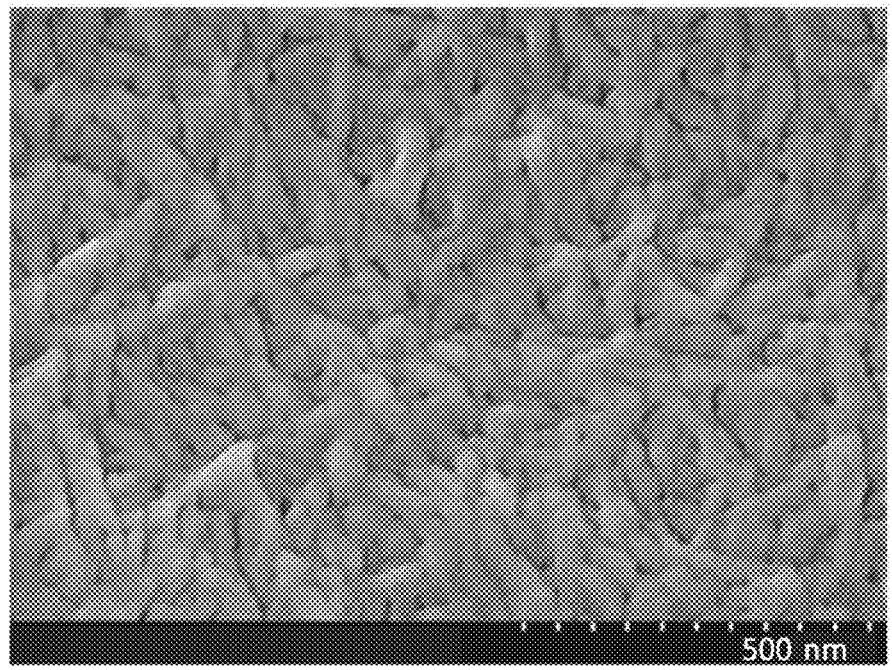
Figure 14A:
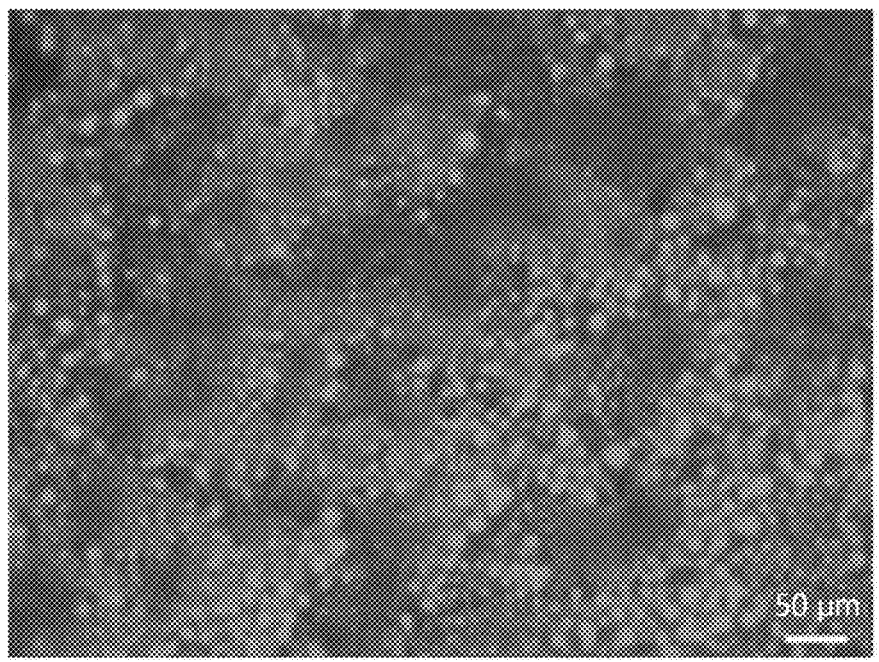
FIGS. 14a to 14c are fluorescence microscopy images of thin emulsion films prepared in Examples 14-16 after heating to 65° C., respectively.
Figure 14B:
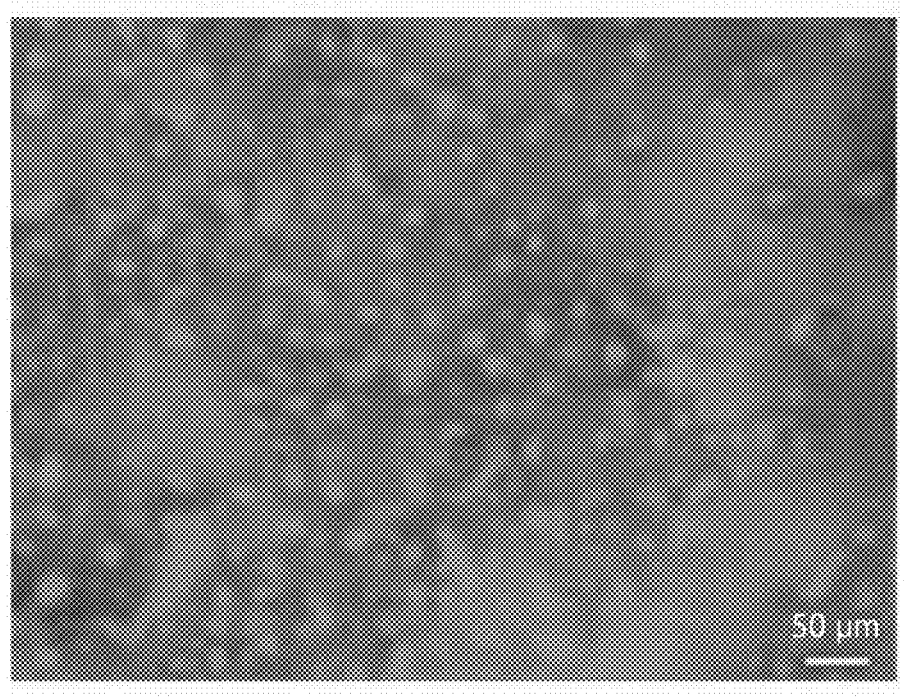
Figure 14C:
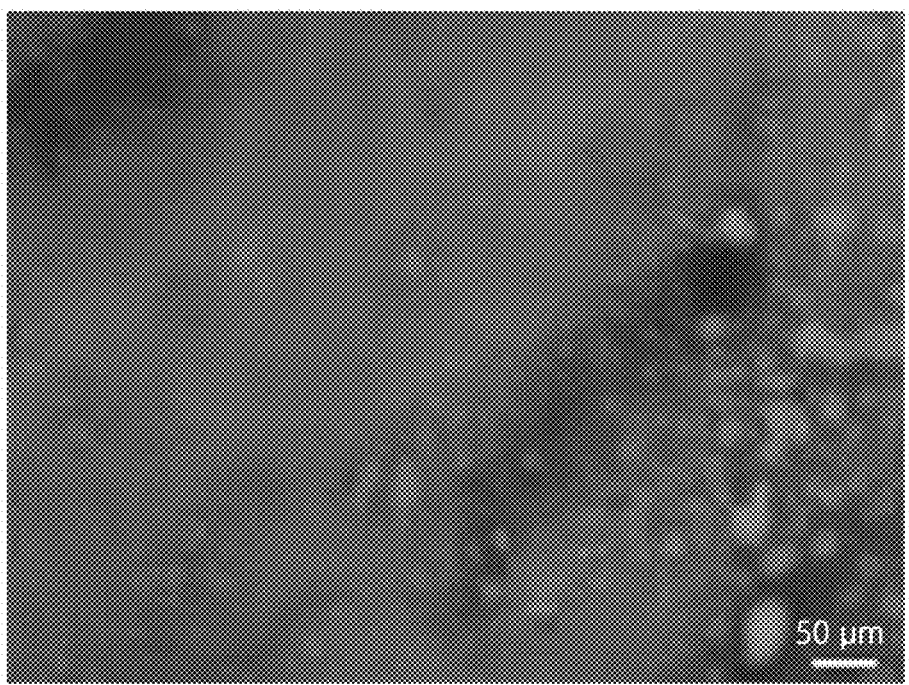

FIGS. 13a to 13c are scanning electron microscopy images of the thin emulsion films prepared in Examples 14-16 after heating to 65° C., respectively. FIGS. 14a to 14c are fluorescence microscopy images of the thin emulsion films prepared in Examples 14-16 after heating to 65° C., respectively.

As shown in FIGS. 13 and 14, the nanofibers were uniformly coated on the surfaces of the thin emulsion films prepared in Examples 14-16 in which each of the composite thin films consisted of the polymer layer, the nanoemulsion layer, the polymer layer, and the nanofiber layer on the substrate.

In the thin emulsion films prepared in Examples 3-10, the domains grew relatively rapidly and the nanoemulsions tended to coalesce. In contrast, the domains grew slowly and were very small and the nanoemulsions were less liable to coalescence in the thin emulsion films of Examples 14-16 because the mechanical properties of the thin emulsion films were enhanced.

Particularly, the thin emulsion films prepared in Examples 14-16 released the drug slowly irrespective of the number of layers of the composite thin films, unlike the thin emulsion films prepared in Examples 3-10. In conclusion, the thin emulsion films prepared in Examples 14-16 can be effectively used in applications where a long drug release time is required.

Figure 15:
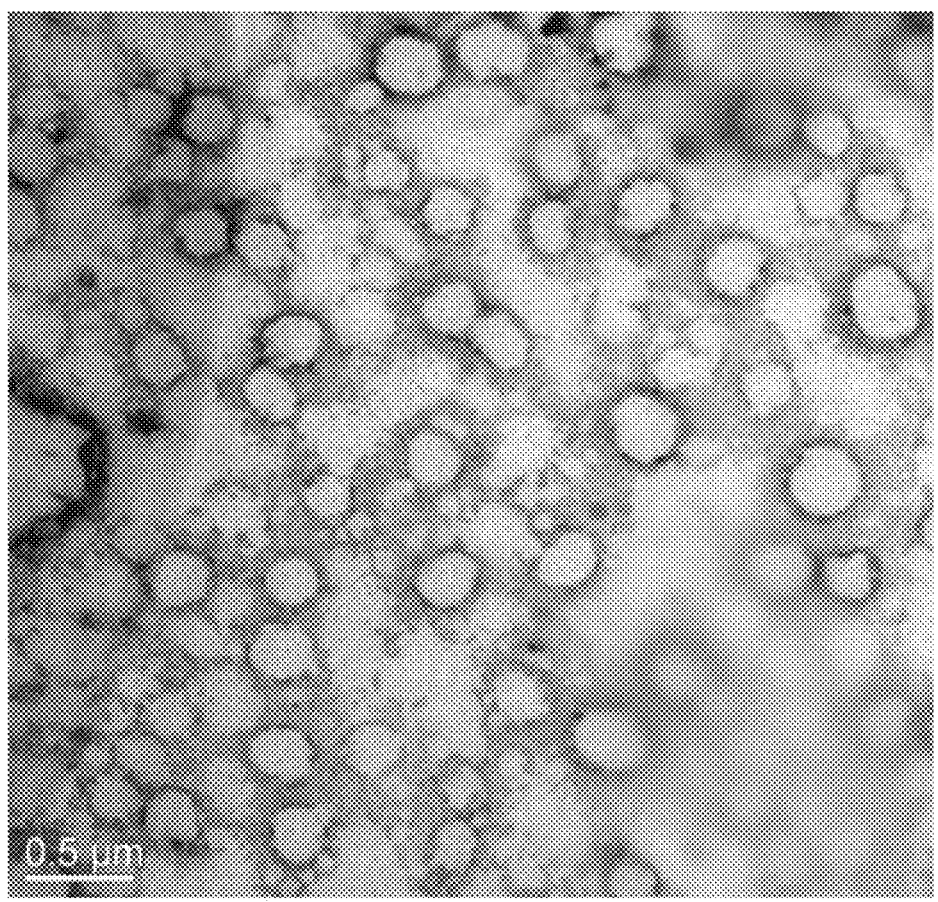
FIG. 15 is a transmission electron microscopy (TEM) image of a thin emulsion film prepared in Example 18 loaded with pyrene as an active substance.
Figure 16:
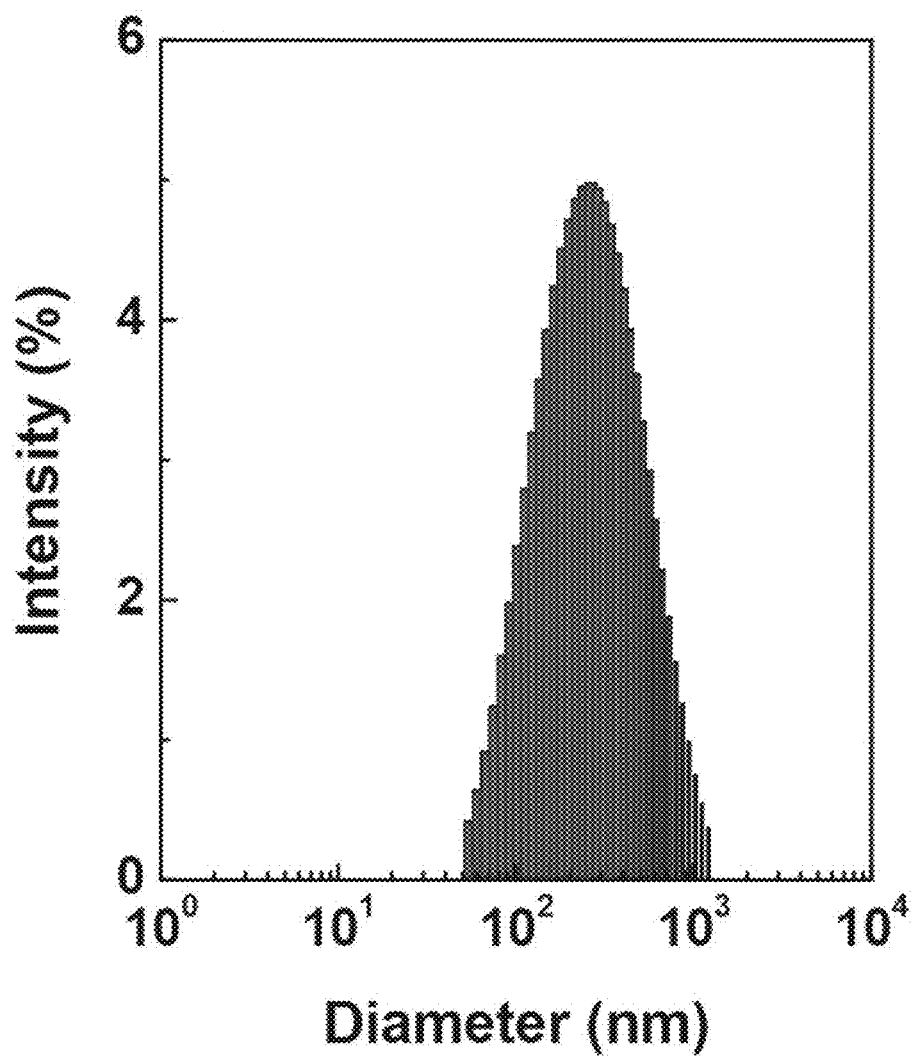
FIG. 16 shows the average particle diameter distribution of nanoemulsions present in a thin emulsion film prepared in Example 18 loaded with pyrene as an active substance.

FIG. 15 is a transmission electron microscopy (TEM) image of the thin emulsion film prepared in Example 18 loaded with pyrene as an active substance. FIG. 16 shows the average particle diameter distribution of nanoemulsions present in the thin emulsion film prepared in Example 18 loaded with pyrene as an active substance.

FIGS. 15 and 16 reveal the presence of the nanoemulsions with uniform size aligned in the thin emulsion film of Example 18, as explained earlier. The nanoemulsions are characterized by their oil and pyrene loadings and the loaded oil was slowly released from the nanoemulsions directly formed into thin films on the substrate in a specific temperature range. This functional effect was not observed in the nanoemulsions before film formation.

It was also confirmed that nanoemulsions loaded with difficult-to-emulsify hydrophobic luminescent pyrene were easily prepared and could be formed into thin films.

Figure 17:
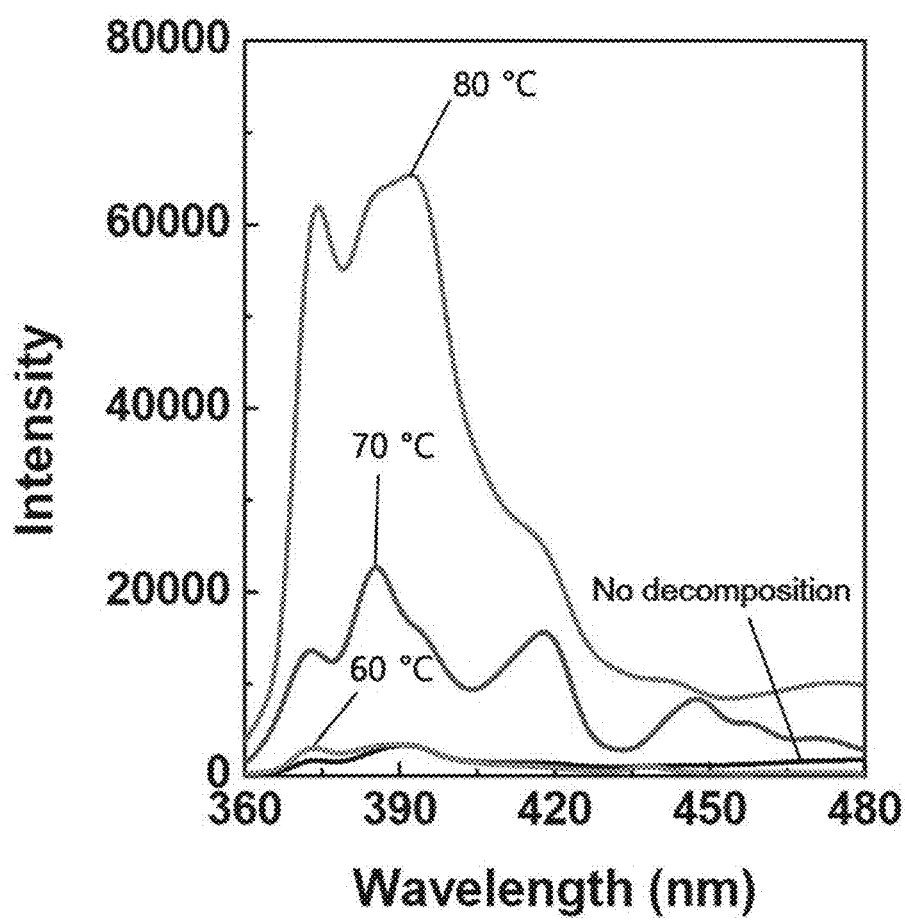
FIG. 17 shows fluorescence spectra of a thin emulsion film prepared in Example 18 at 60, 70, and 80° C.
Figure 18:
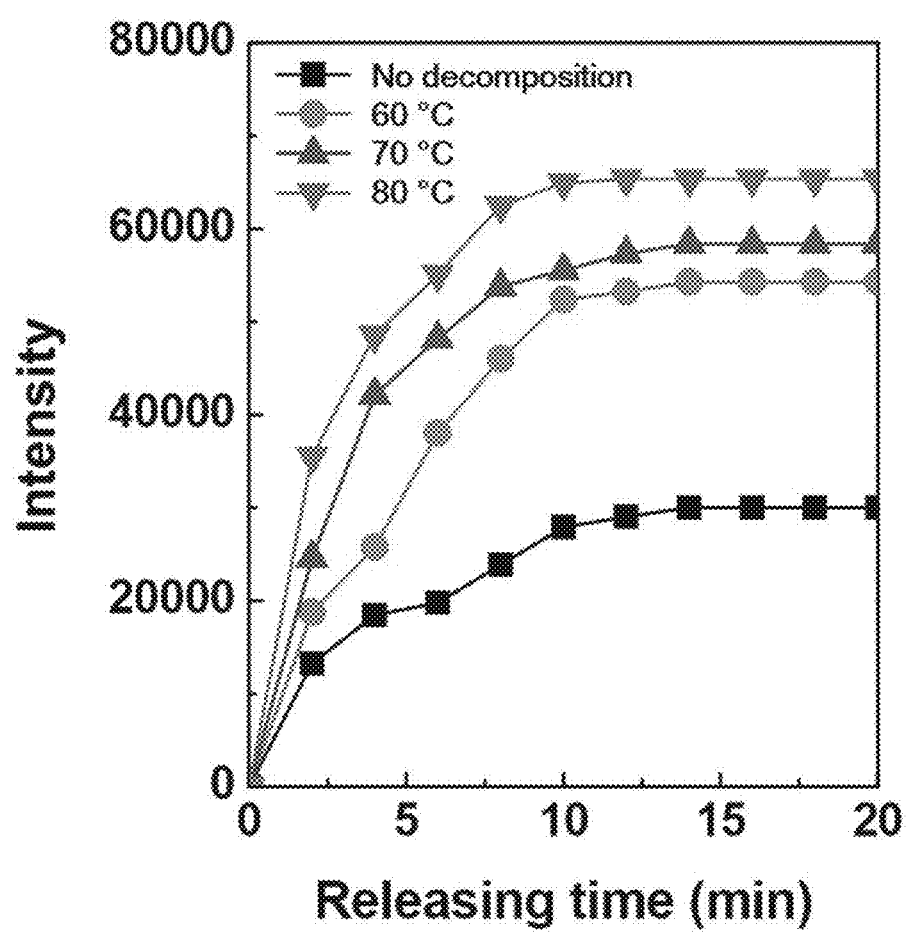
FIG. 18 shows fluorescence spectra of a thin emulsion film prepared in Example 18 at 60, 70, and 80° C., which were measured over time to determine the release times of an active substance from the thin emulsion film.

FIG. 17 shows fluorescence spectra of the thin emulsion film prepared in Example 18 at 60, 70, and 80° C. FIG. 18 shows fluorescence spectra of the thin emulsion film prepared in Example 18 at 60, 70, and 80° C., which were measured over time to determine the release times of the active substance from the thin emulsion film.

Absorption spectral changes were measured to evaluate whether pyrene as an active substance was successfully and stably loaded into the thin emulsion film prepared in Example 18 and whether pyrene was effectively released from the thin emulsion film at specific temperatures (60-80° C.). The fluorescence spectra were recorded at an excitation wavelength of 336 nm using a spectrofluorometer (JASCO FP-6300). Emission spectra were recorded in the wavelength range of 360-480 nm. The fluorescence was measured at room temperature (no decomposition), 60° C., 70° C., and 80° C.

As shown in FIGS. 17 and 18, pyrene was not substantially released from the thin emulsion film of Example 18 at room temperature. In contrast, emission peaks in the range of 360-420 nm for the pyrene monomer were observed at temperatures of 60-80° C.

That is, the thin emulsion film of Example 18 loaded with pyrene as an active substance did not release the active substance at room temperature but slowly released the active substance from when the specific temperature was reached.

What is claimed is:

1. A multilayer thin emulsion film comprising
   a substrate; and
   2 to 100 layers of composite thin films laminated on the substrate to release an active substance in a specific temperature range,
   wherein each of the composite thin films comprise (i) a cross-linkable positively charged polymer layer and (ii) a nanoemulsion layer comprising a plurality of nanoemulsions arrayed on the polymer layer; and
   wherein each of the plurality of nanoemulsions are a spherical particle consisting of (a) a core comprising the active substance and an oil and (b) a shell continuously or discontinuously surrounding the core (a), said shell (b) comprising (b-1) an amphiphilic block copolymer consisting of a biodegradable hydrophobic polymer composed of poly(ester) and a hydrophilic polymer composed of poly(ethylene oxide) and (b-2) lecithin.

2. The multilayer thin emulsion film according to claim 1, wherein the oil is selected from the group consisting of a silicone emulsifier, an O/W emulsifier, an ester oil, a silicone oil, a hydrocarbon oil, a wax, a natural oil, a liquid animal and vegetable oil and fat, and a mixture thereof.

3. The multilayer thin emulsion film according to claim 1, wherein the amphiphilic block copolymer is a polyethylene glycol (PEG)-polycaprolactone (PCL) copolymer having polycaprolactone (PCL) as a hydrophobic block and polyethylene glycol (PEG) as a hydrophilic block.

4. The multilayer thin emulsion film according to claim 3, wherein the amphiphilic block copolymer has a molecular weight of 100 to 100,000 daltons and a degree of polymerization of 1.0 to 1.5.

5. The multilayer thin emulsion film according to claim 3, wherein the polycaprolactone and the polyethylene glycol are present in a weight ratio of 1-1.5:1 in the amphiphilic block copolymer.

6. The multilayer thin emulsion film according to claim 1, wherein the nanoemulsions have an average particle diameter of 0.1 to 100 μm.

7. The multilayer thin emulsion film according to claim 1, wherein the amount of the oil loaded into the core of the nanoemulsions is from 1 to 10 parts by weight, based on 100 parts by weight of the nanoemulsions.

8. The multilayer thin emulsion film according to claim 1, wherein the amount of the cores comprising the active substance and the oil is from 0.2 to 1.0 part by weight, based on 100 parts by weight of the thin emulsion film.

9. The multilayer thin emulsion film according to claim 1, wherein the positively charged polymer is selected from the group consisting of polyallylamine hydrochloride, polyethyleneimine, polylysine, poly(diallyldimethylammonium chloride), and chitosan.

10. The multilayer thin emulsion film according to claim 1, wherein the substrate is negatively charged by plasma treatment.

11. A multilayer thin emulsion film comprising
    a substrate;
    1 to 100 layers of first composite thin films; and
    1 to 100 layers of second composite thin films,
    wherein the first composite thin films and the second composite thin films are laminated alternately with each other on the substrate,
    wherein each of the first composite thin films releases an active substance in a specific temperature range and comprises (i) a cross-linkable cationic polymer layer coated on and (ii) a nanoemulsion layer comprising a plurality of nanoemulsions arrayed on the polymer layer (i),
    wherein each of the second composite thin films is disposed on the first composite thin film and comprises (iii) a cross-linkable cationic polymer layer and (iv) a nanofiber layer formed on the polymer layer (iii), and
    wherein each of the nanoemulsions of the nanoemulsion layer (ii) are a spherical particle consisting of (a) a core comprising the active substance and an oil and (b) a shell continuously or discontinuously surrounding the core, said shell comprising (b-1) an amphiphilic block copolymer consisting of a hydrophobic polymer and a hydrophilic polymer and (b-2) lecithin.

12. The multilayer thin emulsion film according to claim 11, wherein the oil is selected from the group consisting of a silicone emulsifier, an O/W emulsifier, an ester oil, a silicone oil, a hydrocarbon oil, a wax, a natural oil, a liquid animal and vegetable oil and fat, and a mixture thereof.

13. The multilayer thin emulsion film according to claim 11, wherein the amphiphilic block copolymer is a polyethylene glycol (PEG)-polycaprolactone (PCL) copolymer having polycaprolactone (PCL) as a hydrophobic block and polyethylene glycol (PEG) as a hydrophilic block.

14. The multilayer thin emulsion film according to claim 13, wherein the amphiphilic block copolymer has a molecular weight of 100 to 100,000 daltons and a degree of polymerization of 1.0 to 1.5.

15. The multilayer thin emulsion film according to claim 13, wherein the polycaprolactone and the polyethylene glycol are present in a weight ratio of 1-1.5:1 in the amphiphilic block copolymer.

16. The multilayer thin emulsion film according to claim 11, wherein the nanoemulsions have an average particle diameter of 0.1 to 100μm.

17. The multilayer thin emulsion film according to claim 11, wherein the amount of the oil loaded into the core of the nanoemulsions is from 1 to 10 parts by weight, based on 100 parts by weight of the nanoemulsions.

18. The multilayer thin emulsion film according to claim 11, wherein the amount of the cores comprising the active substance and the oil is from 0.2 to 1.0 part by weight, based on 100 parts by weight of the thin emulsion film.

19. The multilayer thin emulsion film according to claim 11, wherein the positively charged polymer is selected from the group consisting of polyallylamine hydrochloride, polyethyleneimine, polylysine, polydimethyldiallylammonium chloride, and chitosan.

20. A method for preparing a multilayer thin emulsion film, comprising: I) mixing a dispersed phase solution with an aqueous suspension to prepare a mixture solution comprising nanoemulsions; II) modifying the surface of a substrate to negatively charge the substrate surface; III) immersing the substrate in a solution comprising a positively charged polymer to form a polymer layer; and IV) withdrawing the substrate from the solution and immersing the withdrawn substrate in the mixture solution comprising nanoemulsions to form a nanoemulsion layer on the polymer layer.

* * * * *